(12) United States Patent
Pardes et al.

(10) Patent No.: US 7,874,467 B2
(45) Date of Patent: Jan. 25, 2011

(54) METERED DROP PUSH BUTTON DISPENSER SYSTEM

(75) Inventors: Greg Pardes, New York, NY (US);
Stewart Swiss, Lloyd Harbor, NY (US);
Paul Mulhauser, New York, NY (US);
Lyndon T. Treacy, Long Island City, NY (US)

(73) Assignee: ReSeal International Limited Partnership, New York, NY (US)

( * ) Notice: Subject to any disclaimer, the term of this patent is extended or adjusted under 35 U.S.C. 154(b) by 219 days.

(21) Appl. No.: 12/274,137

(22) Filed: Nov. 19, 2008

(65) Prior Publication Data

US 2009/0236374 A1 Sep. 24, 2009

Related U.S. Application Data

(63) Continuation-in-part of application No. PCT/US2008/075443, filed on Sep. 5, 2008, which is a continuation-in-part of application No. 11/949,154, filed on Dec. 3, 2007, now Pat. No. 7,513,396, which is a continuation of application No. 11/267,868, filed on Nov. 3, 2005, now Pat. No. 7,306,129, application No. 12/274,137, which is a continuation-in-part of application No. 12/092,689, filed as application No. PCT/US2006/42940 on Nov. 3, 2006, which is a continuation-in-part of application No. 11/267,868, application No. 12/274,137, which is a continuation-in-part of application No. 12/092,691, filed as application No. PCT/US2006/43113 on Nov. 3, 2006, which is a continuation-in-part of application No. 11/267,868.

(60) Provisional application No. 60/970,588, filed on Sep. 7, 2007, provisional application No. 60/823,452, filed on Aug. 24, 2006, provisional application No. 60/783, 451, filed on Mar. 17, 2006, provisional application No. 60/783,569, filed on Mar. 17, 2006, provisional application No. 60/840,377, filed on Aug. 24, 2006.

(51) Int. Cl.
*B65D 5/72* (2006.01)

(52) U.S. Cl. .................. 222/494; 222/105; 222/212; 222/213; 222/321.7; 222/326; 222/380; 222/490; 137/853; 604/213

(58) Field of Classification Search .......... 222/490–491, 222/494–497, 321.7, 380, 420–422, 206–207, 222/212–215, 105, 107, 630–631, 183, 326, 222/386, 94–95, 325, 327, 321.8, 321.9; 137/852–853; 604/298, 213
See application file for complete search history.

(56) References Cited

U.S. PATENT DOCUMENTS 2,715,980 A * 8/1955 Frick ........................ 222/183

(Continued)

*Primary Examiner*—Frederick C. Nicolas
(74) *Attorney, Agent, or Firm*—Kramer Levin Naftalis & Frankel LLP

(57) ABSTRACT

A reusable continuously sealing metered dosing one-way valve assembly and delivery system flows a premeasured amount of a sterile flowable substance from a source which is coupled to an actuator assembly to an outlet orifice and prevents any backflow of contaminants through the continuously sealing one way valve assembly when the flowable substance ceases to flow. The valve assembly includes an elastomeric membrane which aids in preventing any backflow of contaminants when dispensing of the flowable substance is stopped. Multiple dosing of preservative-free flowable substance is provided.

19 Claims, 22 Drawing Sheets

U.S. PATENT DOCUMENTS

| | | | | |
|---|---|---|---|---|
| 3,124,275 A * | 3/1964 | Lake | | 222/182 |
| 3,506,163 A * | 4/1970 | Rauh et al. | | 222/212 |
| 3,739,652 A * | 6/1973 | Caldwell et al. | | 74/421 A |
| 4,349,133 A * | 9/1982 | Christine | | 222/183 |
| 4,397,132 A * | 8/1983 | Pardes et al. | | 53/471 |
| 4,413,757 A * | 11/1983 | Adler | | 222/105 |
| 4,415,121 A * | 11/1983 | Berger et al. | | 239/229 |
| 4,421,510 A * | 12/1983 | Ahlbeck | | 604/323 |
| 4,846,810 A * | 7/1989 | Gerber | | 604/247 |
| 4,898,306 A * | 2/1990 | Pardes | | 222/206 |
| 5,080,138 A * | 1/1992 | Haviv | | 137/853 |
| 5,092,855 A * | 3/1992 | Pardes | | 604/247 |
| 5,190,190 A * | 3/1993 | Fudalla | | 222/105 |
| 5,305,786 A * | 4/1994 | Debush | | 137/512.3 |
| 5,836,484 A * | 11/1998 | Gerber | | 222/494 |
| 6,325,253 B1 * | 12/2001 | Robinson | | 222/212 |
| 6,386,395 B1 * | 5/2002 | Lunghetti | | 222/213 |
| 6,536,631 B1 * | 3/2003 | Nickels et al. | | 222/212 |
| 6,662,977 B2 * | 12/2003 | Gerber et al. | | 222/494 |
| 6,695,173 B1 * | 2/2004 | Fontana | | 222/212 |
| 6,766,816 B2 * | 7/2004 | Secondo | | 137/1 |
| 6,896,151 B1 * | 5/2005 | Robinson | | 222/1 |
| 6,997,219 B2 * | 2/2006 | Py et al. | | 141/314 |
| 7,077,176 B2 * | 7/2006 | Py | | 141/301 |
| 7,226,237 B2 * | 6/2007 | Ceccarelli | | 404/6 |
| 7,306,129 B2 * | 12/2007 | Swiss et al. | | 222/494 |
| 7,513,396 B2 * | 4/2009 | Pardes et al. | | 222/494 |

* cited by examiner

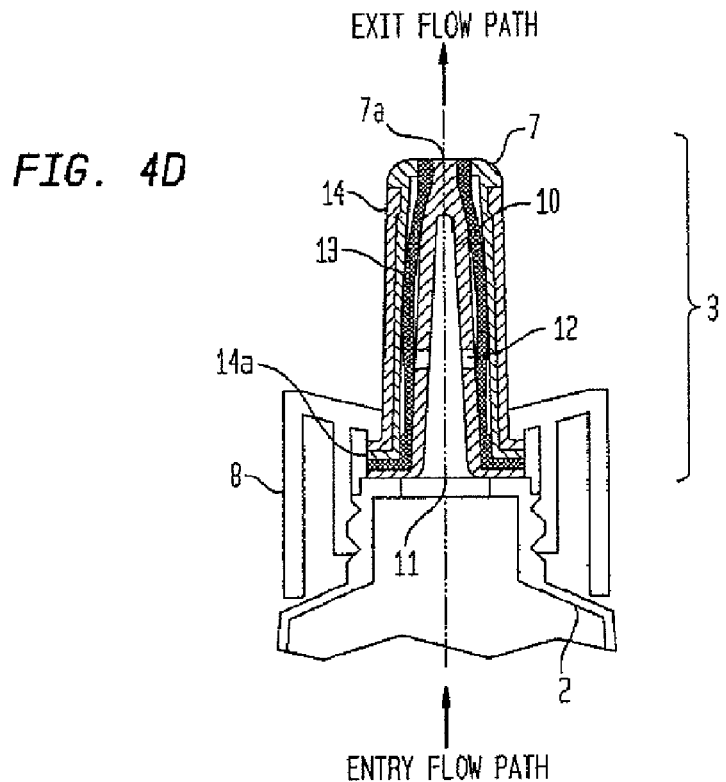
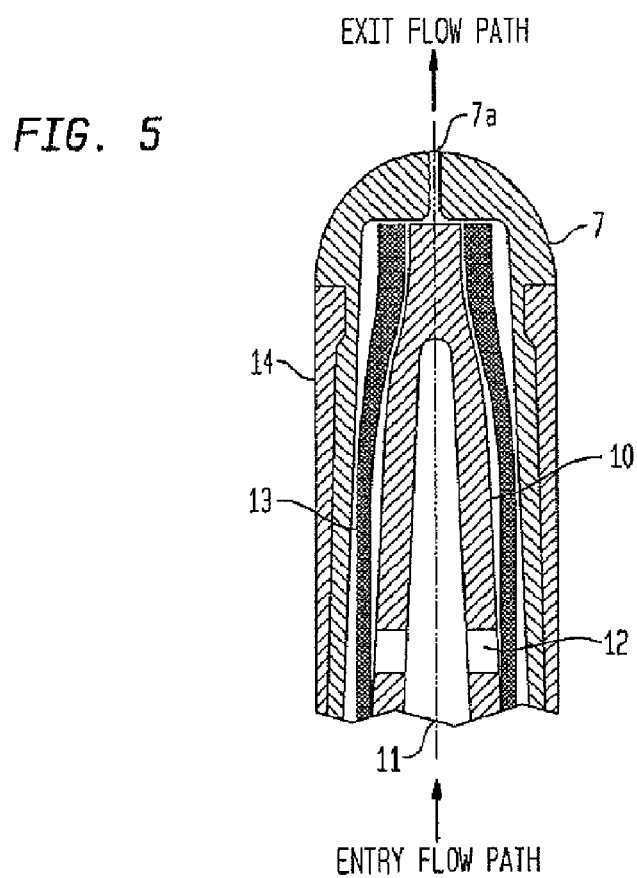

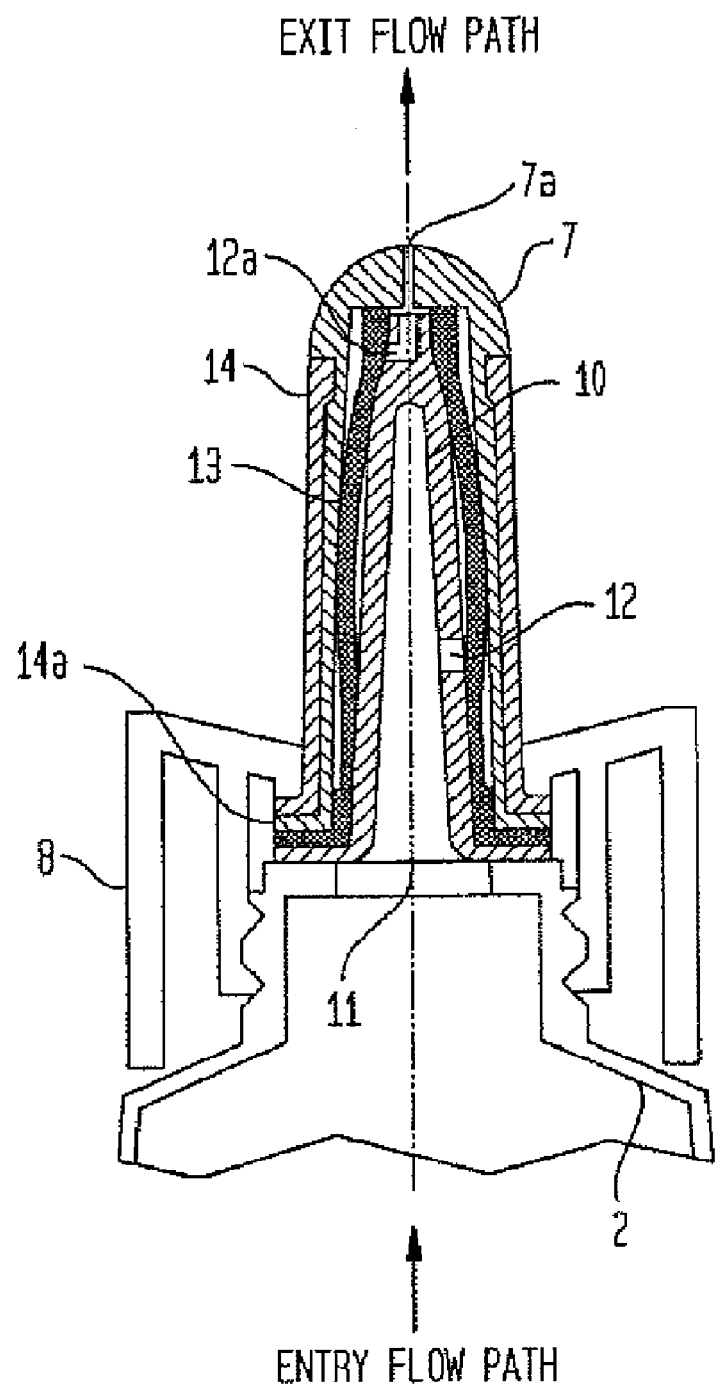

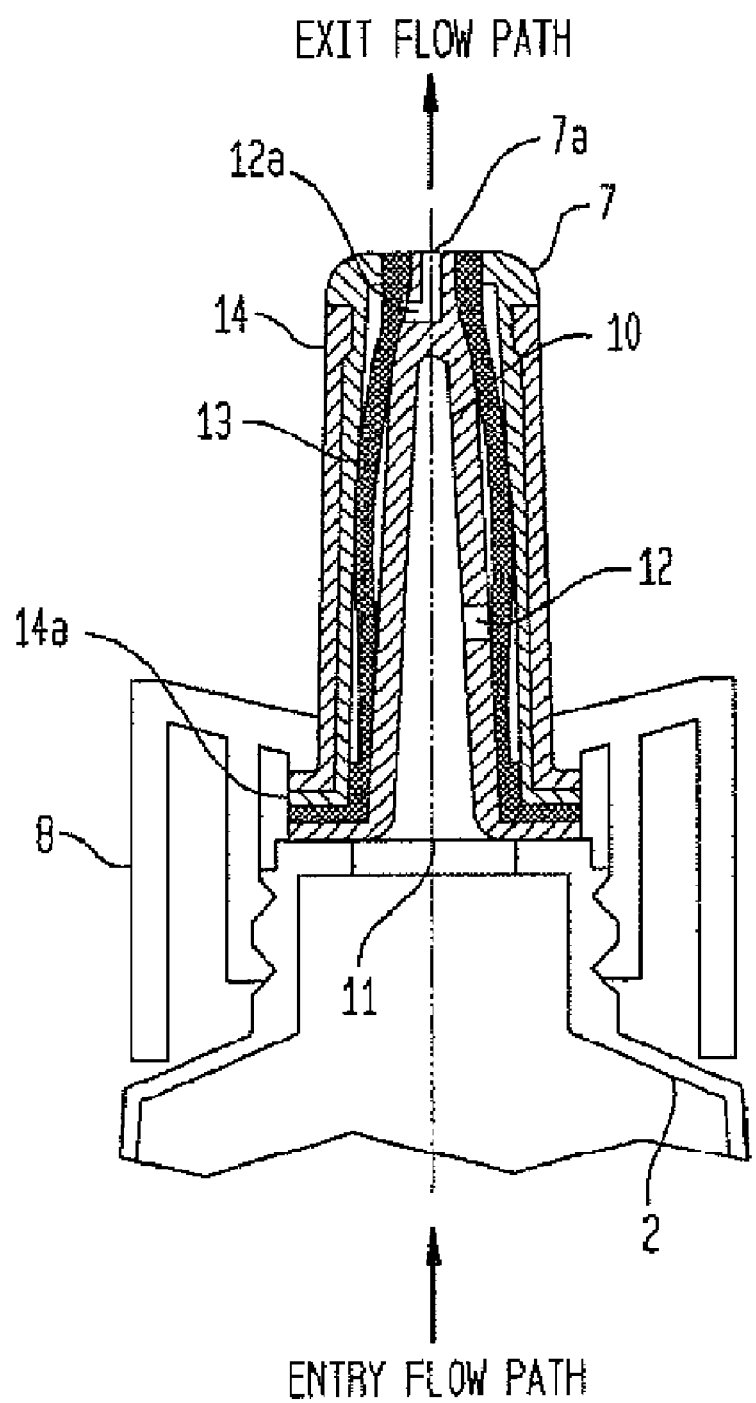

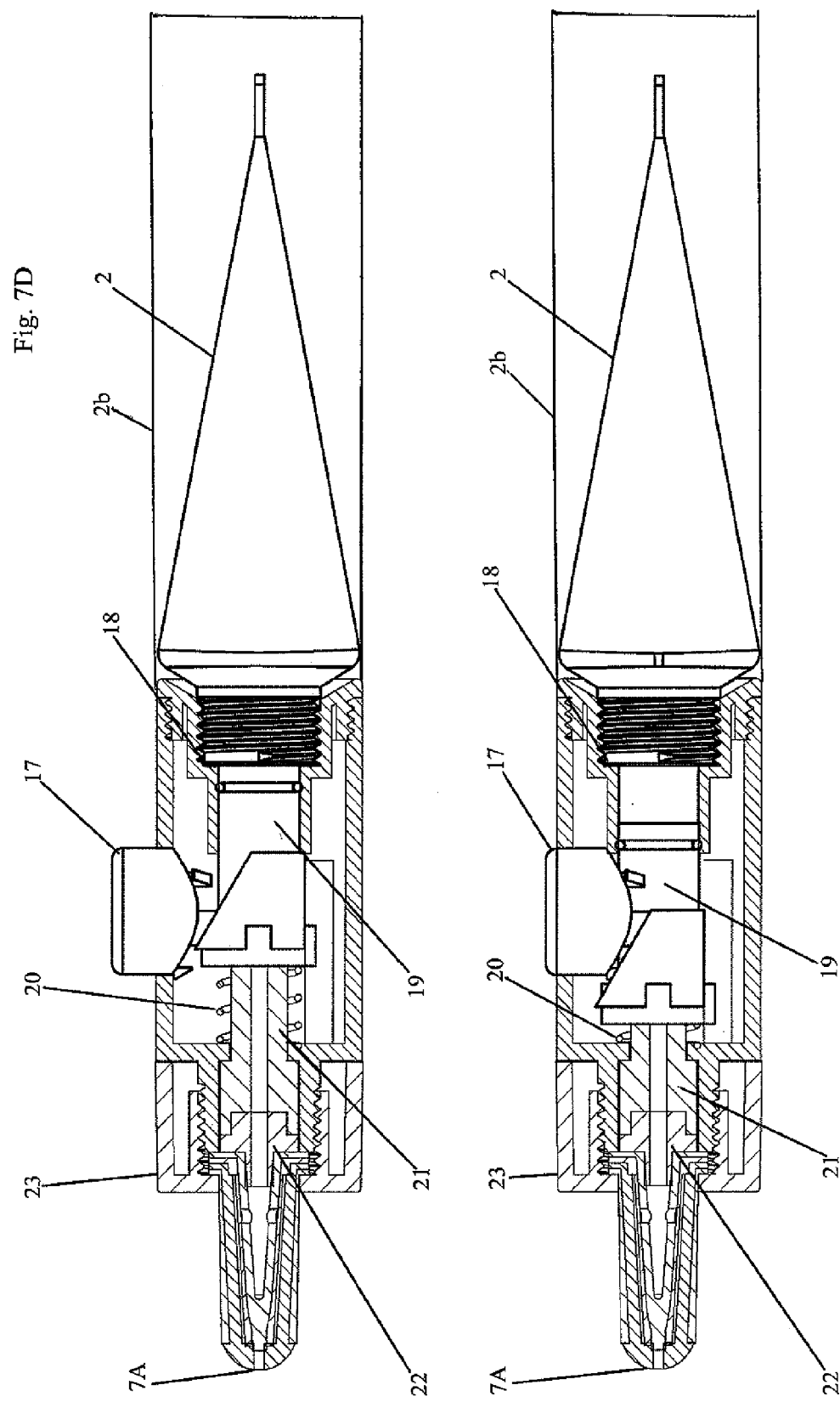

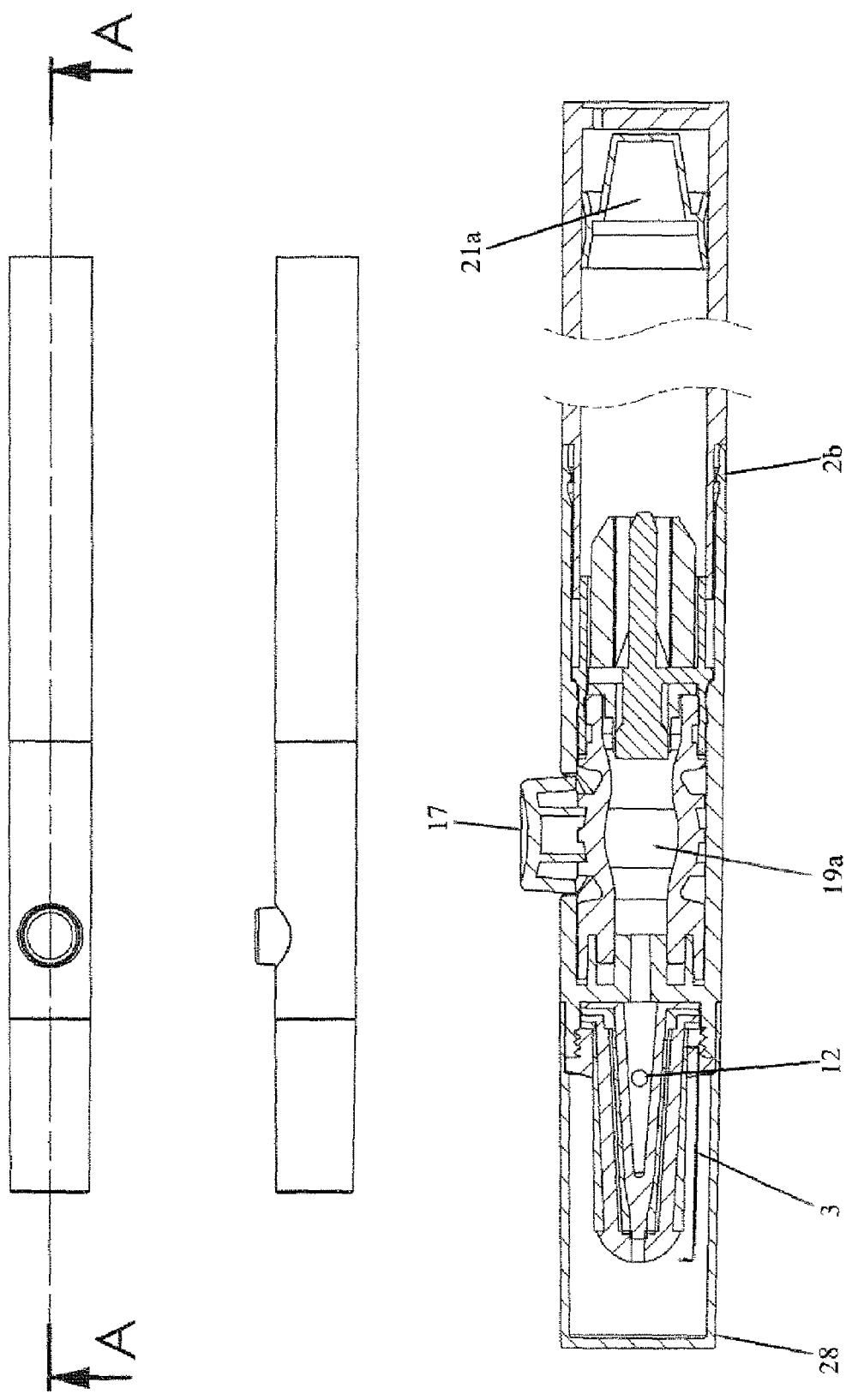

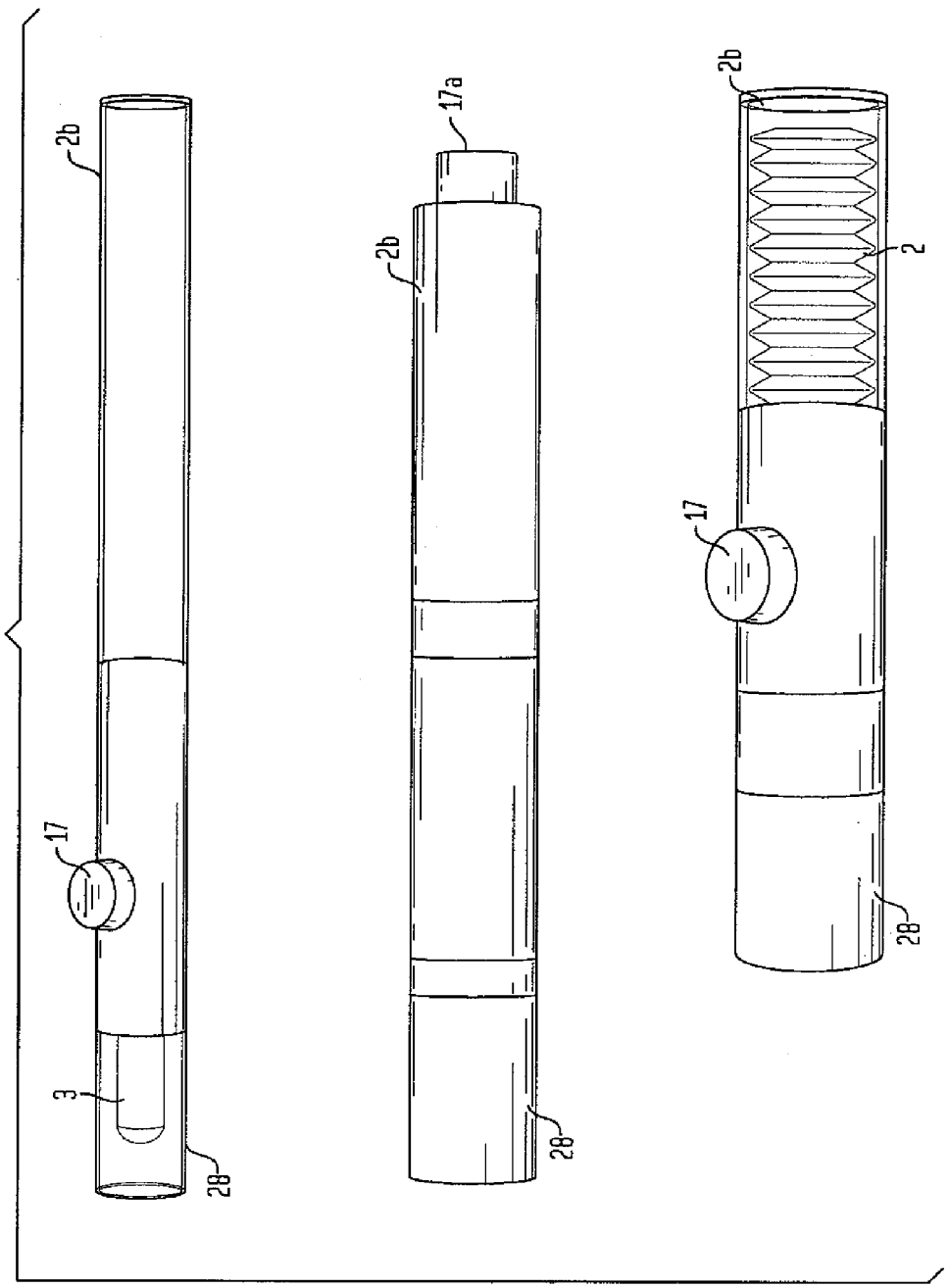

METERED DROP PUSH BUTTON DISPENSER SYSTEM

CROSS REFERENCE TO RELATED APPLICATIONS

This application is a Continuation-in-part of PCT International Application No. PCT/US08/75443, filed Sep. 5, 2008, which claims the priority of U.S. Provisional Patent Application No. 60/970,588, filed Sep. 7, 2007. This application is also a Continuation-in-part of U.S. patent application Ser. No. 11/949,154, filed Dec. 3, 2007, now pending, which is a continuation of U.S. patent application Ser. No. 11/267,868, now U.S. Pat. No. 7,306,129. This application is also a Continuation-in-part of U.S. patent application Ser. No. 12/092,689, filed on May 5, 2008, now pending, which is a U.S. National Phase application of PCT International Application No. PCT/US06/42940, filed Nov. 3, 2006, which claims the priority of U.S. Provisional Patent Application No. 60/823,452, filed Aug. 24, 2006 and which is also a Continuation-in-part of U.S. patent application Ser. No. 11/267,868, now U.S. Pat. No. 7,306,129. This application is also a Continuation-in-part of U.S. patent application Ser. No. 12/092,691, filed on May 5, 2008, now pending, which is a U.S. National Phase application of PCT International Application No. PCT/US06/43113, filed Nov. 3, 2006, which claims the priority of U.S. Provisional Patent Application Nos. 60/840,377, filed Aug. 24, 2006; 60/783,451, filed Mar. 17, 2006; 60/783,569, filed Mar. 17, 2006 and which is also a Continuation-in-part of U.S. patent application Ser. No. 11/267,868, now U.S. Pat. No. 7,306,129. All of the aforementioned patent applications are hereby incorporated by reference in their entirety.

FIELD OF THE INVENTION

The present invention is directed to a dispensing or delivery system including a continuously sealing one way valve assembly for dispensing a sterile flowable substance, which can be preservative free or may include preservatives, while preventing a backflow of contaminants into the source of the flowable substance. The dispensing or delivery system includes, for example, a valve assembly enclosed by a pressure displaceable flexible member or elastomeric member for effecting the passage of the flowable substance to a controllable outlet, while preventing any backflow to the source of the flowable substance after dispensing individual portions or doses of the flowable substance. Such valve assembly works in conjunction with of a metered drop push button dispenser to dispense individual portions or doses of the flowable substance.

BACKGROUND INFORMATION

In the past, to maintain the flowable substance free of contaminants, preservatives have been mixed in with the flowable substance in the reservoir from which it is to be dispensed. The use of preservatives tends to be detrimental to users and often limits the effectiveness of the flowable substance, particularly when the flowable substance is a pharmaceutical such as an eye care solution, an intranasal drug, cosmetic treatment or skin treatment product. This group of prescription and nonprescription medications are often formulated with preservatives in multi-dose formats. The flowable substance may also be a food stuff, a beverage, a nutraceutical or cosmeceutical product.

Another consideration is the ability of the valve assembly to deliver a selected amount of the flowable substance to the outlet without causing any damage to the user, such as when applying an eye care solution directly into the eye.

In the past, flexible membranes have been used to control the flow of the flowable substance to the valve assembly outlet while preventing any backflow to the source of the flowable substance. However such valves, such as the valve described in U.S. Pat. No. RE34,243, which is incorporated by reference herein in its entirety, describe the use of O-rings in conjunction with a uniformly thick flexible membrane to effect a seal. Other valve assemblies also used cylindrical parts which required, for example, sliding the pretensioned flexible membrane over the straight sided core during assembly, preventing automated high speed assembly. Still other valve assemblies require squeezing a reservoir of flowable substance in order to dispense the flowable substance. Such squeezing can be difficult for the very young or very old and for physically challenged or disabled individuals. Therefore, an effectively designed, easy to operate valve assembly and metered dispenser system for preservative free flowable substances is desirable. Further, such a system is able to be manufactured, for example via high speed automated production, and which limits the costs of manufacture by reducing component parts and allowing the use of high speed automated production is further desired. Thus, the present invention provides metered dispensing and storage of preservative free flowable substances while preventing contamination, all of which is not provided in the prior art.

SUMMARY OF THE INVENTION

According to an exemplary embodiment of the present invention, a dispensing or delivery system conveys a flowable substance from a closed source, such as a collapsible reservoir within a rigid container or a rigid reservoir, while preventing any backflow of oxygen or other contaminants from the ambient atmosphere through the valve assembly and into the source of the flowable substance after a portion of the substance has been dispensed. Such a device can be formed from a valve assembly, an actuator assembly and a source for flowable substance.

The collapsible reservoir can be, for example, a bellows type reservoir, a collapsible tube, an internal bag or other type of suitable reservoir designed to dispense practically all of its contents. According to an exemplary embodiment of the present invention, the dispensing delivery system has a normally closed controllable outlet orifice for dispensing a controlled amount of the flowable substance out of the valve assembly. The reservoir is in sealed contact with the valve assembly so that its contents do not receive any contaminants when the flowable substance is dispensed.

Dispensation of the flowable substance is effected by applying pressure to a flowable substance in a reservoir directly or through a pump so that its contents flow to and through the valve assembly. The contents may be, for example, a pharmaceutical, such as an eye care solution or other substance which is to be kept free of contaminants during dispensing. According to an exemplary embodiment of the present invention, a multiple number of dispensed amounts can be provided while keeping the undispensed flowable substance preservative-free. Other flowable substances which are preservative-free can be food stuffs, juices or beverages, cosmetics, or other flowable substances intended to be maintained free of preservatives and contaminants, notwithstanding multiple uses of the dispenser delivery system. The flowable substance reservoir is protected by a housing so that pressure is not accidentally applied.

The valve assembly includes, for example, an axially extending structure open to the dispenser or reservoir of the flowable substance. The valve assembly can be formed of an axially extending inner core open to the reservoir and formed of a rigid plastic component. The interior of the core can have a passageway for receiving the flowable substance from the reservoir. At least one port extending from the passageway can be provided and affords an opening for conveying the flow substance out of the inner core. The inner core can be designed with a substantially tapered or substantially conical shape.

An axially extending flexible membrane tightly encloses the inner core and covers the outlet end of the port through the inner core. The flexible membrane moves outwardly from the inner core when the flowable substance is pressurized and passes through the port and flows toward the outlet end of the flexible membrane. The flexible membrane is structured such that it is, for example, thicker at the end closest to the valve opening, e.g. the flexible membrane is not uniformly thick along its length. This thickness allows the valve to seal at the thicker end first. Alternatively, even if the membrane was of uniform thickness, the elasticity of the membrane can be varied so that the portion of the membrane closest to the valve opening is less elastic, resulting in the portion of the membrane closest to the valve opening closing first.

In exemplary embodiments, the flexible membrane and, as described above, the inner core, are of a substantially tapered or substantially conical shape, allowing for the rapid assembly and nesting of the flexible membrane over the inner core.

A valve cover located laterally outwardly from the flexible membrane ends at the controllable outlet orifice. The pressurized flowable substance travels between the radially outwardly extended flexible membrane and the outer surface of the inner core and flows to the controllable outlet orifice. The outlet orifice provides for controlled amounts of the flowable substance to be dispensed. An over cap covers the exterior of the valve cover to protect the valve assembly during storage. A collar can join the valve assembly to the reservoir and afford a sealed arrangement preventing any flow of contaminants into the reservoir. The collar and the neck area of the reservoir are designed with locking features that permit the override of the collar during assembly but subsequently prevent the unscrewing and disassembly of the collar and the opening of and likely contamination of the system.

In exemplary embodiments, metered dispensing is achieved by an actuator assembly, for example, through the placement of a check valve and chamber between the reservoir and valve assembly or through the use of a check valve and chamber alone. Such a configuration may be push button actuated, which also allows for significantly easier dispensing in terms of the force required to be exerted by the user to dispense flowable substance.

In exemplary embodiments, one or more, or all, components of the valve assembly, actuator assembly and source can have integrated, impregnated, coated, or otherwise placed within them anti-microbial ingredients or water repellant ingredients.

The various features of novelty which characterize the present invention are pointed out with particularity in the claims annexed to and forming a part of this disclosure. For a better understanding of the present invention, its operation, advantages and specific objects attained by its use, reference should be had to the accompanying drawings and descriptive matter in which preferred embodiments of the invention are illustrated and described.

BRIEF DESCRIPTION OF THE DRAWINGS

FIG. 4D is an enlarged axially extending partial view of the continuously sealing one way valve assembly where the opening in the soft cover contains a portion of the flexible membrane and inner core of the valve assembly according to an exemplary embodiment of the present invention.

FIG. 5 is an enlarged partial axially extending view of the continuously sealing one way valve assembly shown in FIGS. 4B and 4C according to an exemplary embodiment of the present invention.

FIG. 6A is an axially extending partial view of the continuously sealing one way valve assembly with one port and an outlet port according to an exemplary embodiment of the present invention.

FIG. 6B is an enlarged axially extending partial view of the continuously sealing one way valve assembly with one port and an outlet port according to an exemplary embodiment of the present invention.

FIG. 7D is a cut away of an exemplary metered push button dispenser system depicting the operation of the system.

FIG. 8B is an axially extending view of a metered push button dispenser system according to an exemplary embodiment of the present invention.

FIG. 10B depicts metered push button delivery or dispensing systems with rigid reservoirs according to exemplary embodiments of the present invention.

DETAILED DESCRIPTION OF THE INVENTION

Figure 1:
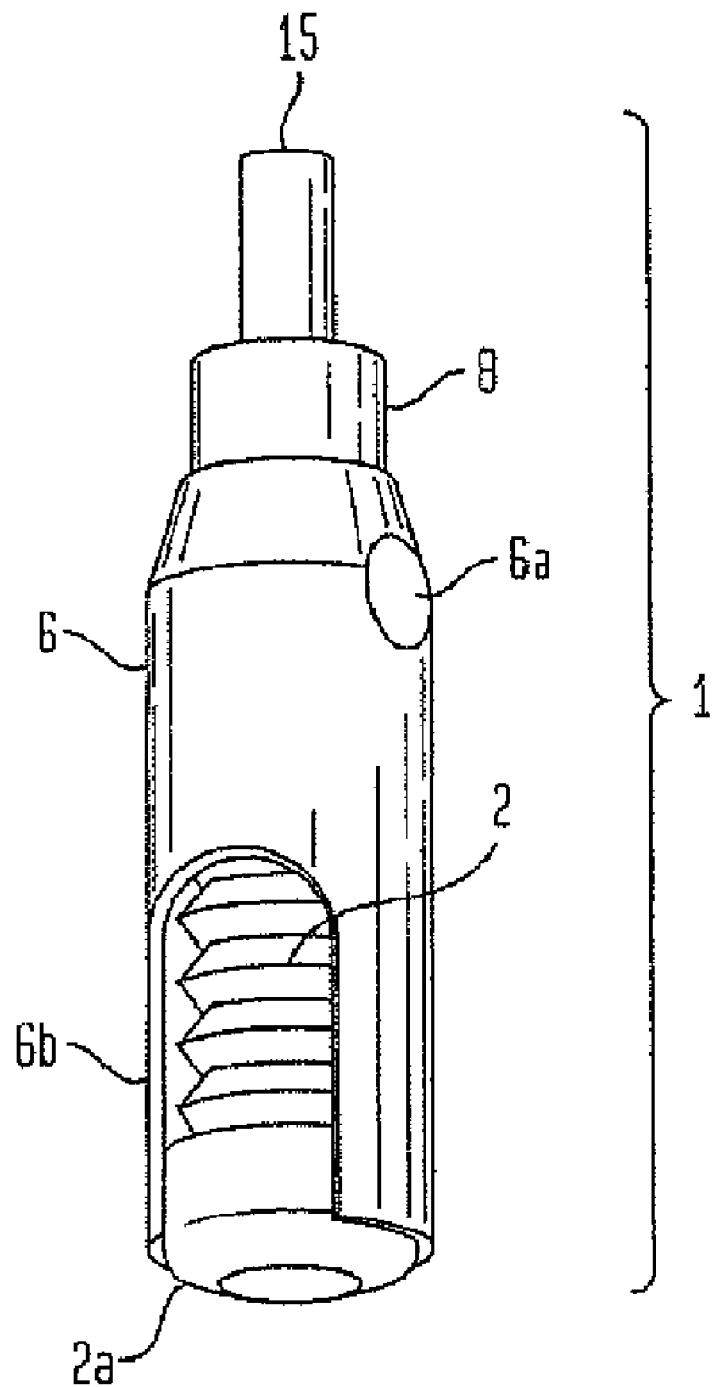
FIG. 1 is an axially extending view of a dispensing or delivery system according to an exemplary embodiment of the present invention.
Figure 2A:
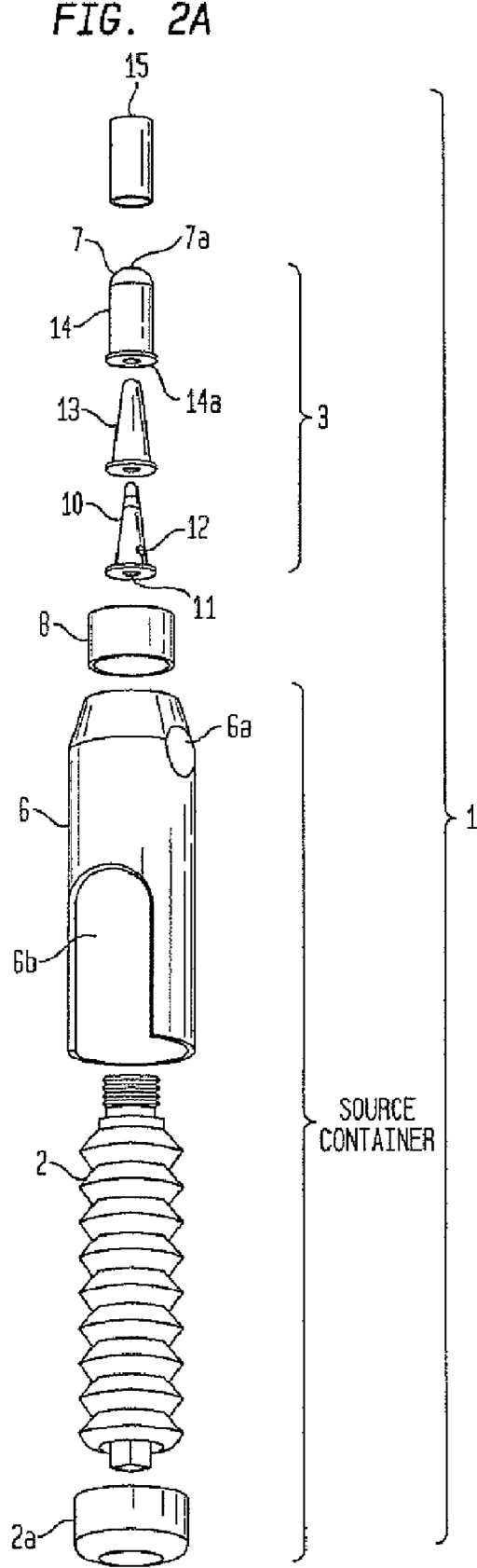
FIG. 2A is an exploded view of a dispensing or delivery system such as that shown in FIG. 1 according to an exemplary embodiment of the present invention.
Figure 2B:
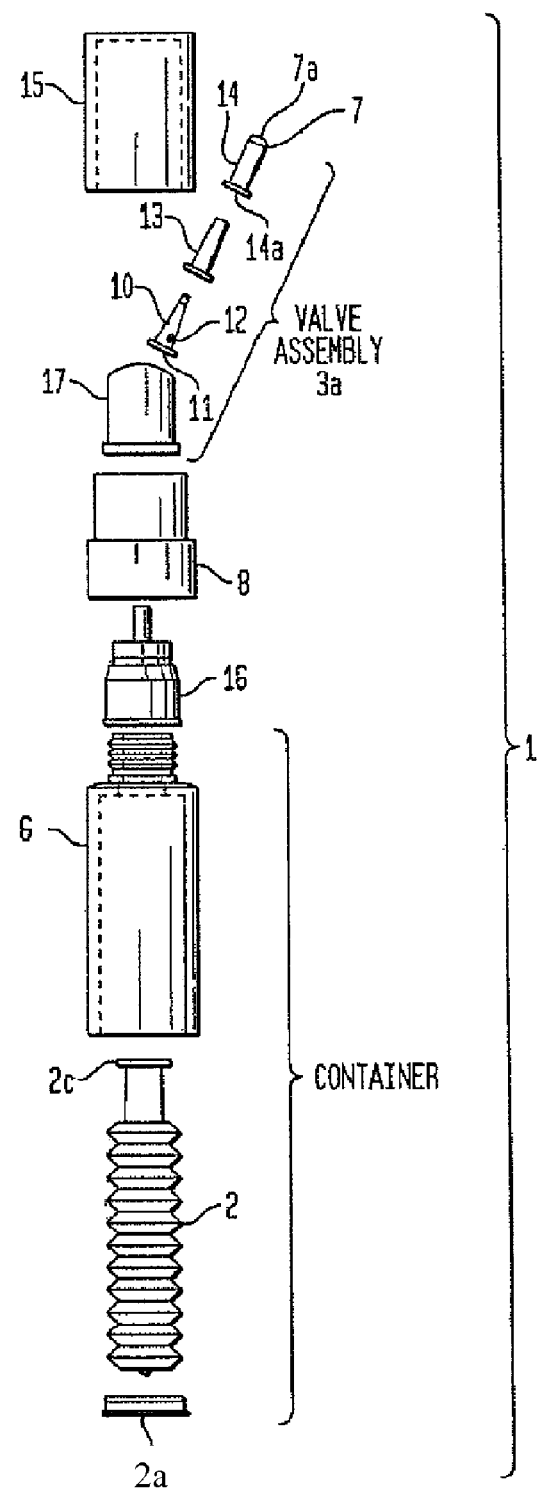
FIG. 2B is an exploded view of a dispensing or delivery system such as that shown in FIG. 1 according to an exemplary embodiment of the present invention which includes a pump for dispensing flowable substance.

As shown in FIGS. 1, 2A and 2B, dispensing or delivery system 1 according to exemplary embodiments of the present invention is comprised of a bellows reservoir or source 2 located within a housing 6. The housing 6 holds reservoir 2 of flowable substance, preferably a sterile or pure flowable substance, a valve assembly 3 (shown in detail in FIGS. 2A, 2B and 4A-D) for conveying the flowable substance from the reservoir 2 to an outlet when pressure is applied to the flowable substance in the reservoir 2 or to an actuator 2a connected to the reservoir 2. An over cap 15 covers the valve assembly 3 to prevent damage to the exterior of the valve assembly 3. The housing 6 has surfaces 6a for holding the assembly. A collar 8 connects the valve assembly 3 to the reservoir 2 affording a sealed connection so that ambient contaminants cannot pass into the reservoir 2.

Referring again to FIGS. 1, 2A and 2B, the bellows reservoir 2 is sufficiently large to allow for multiple doses to be dispensed from the reservoir and collapses when pressure is applied to the flowable substance in the reservoir. Other suitable reservoirs may be used, such as a collapsible tube or an internal bag in a reservoir that permit multi-dose dispensation of the flowable substance. The valve assembly 3 and collar 8 preferably prevents air or other contamination from entering the reservoir during and following the dispensing procedure.

Referring yet again to FIGS. 1, 2A and 2B, the bellows reservoir or source 2 is laterally enclosed, for example, by an axially extending housing 6 to prevent the accidental application of pressure to the reservoir. A slot 6b extending axially in the housing 6 permits a user to gain access to an actuator 2a of the reservoir as the flowable substance is pressed out. The housing 6 has surfaces 6a for holding the housing when the flowable substance is being dispensed.

Referring now to FIGS. 2A and 2B, the valve assembly 3 has valve cover 14 which encircles the flexible membrane 13. The valve assembly 3 is comprised of an inner core 10, an axially extending blind passageway 11, ports 12, a flexible membrane 13, a valve cover 14 with a flange 14a, and a soft cover 7 with a controllable outlet orifice 7a (all of which are described in greater detail below in connection with the descriptions of FIGS. 4A-D). While the flexible membrane 13 is hollow so as to accommodate the inner core 10, it is understood that when assembled with the device, it is filled with the inner core 10 such that no gap remains when the valve assembly is at rest.

The end of the valve cover 14 adjacent the reservoir 2 has a radially outwardly extending flange 14a bearing against the flange at the end of the flexible membrane effecting the seal for the valve assembly at the opening from the reservoir 2. The opening or neck area of reservoir 2 seals against flange 14a, for example, by way of a screw thread which mates with the collar 8. Alternatively, or in addition, the collar 8 and the opening or neck area of the reservoir 2 are designed with locking features that permit the override of the collar 8 during assembly but subsequently prevent the unscrewing and disassembly of the collar 8 and the opening of the system. This prevents any unintended contamination by the consumer and also eliminates the possibility of refilling the system.

Referring now especially to FIG. 2B, in an exemplary embodiment suitable for pumping flowable substance, a pump assembly 16 is joined to a valve assembly 3a and to a reservoir 2 and bottle 6b. The collar 8 surrounds the connection between the pump assembly 16 and valve assembly 3a. The pump assembly 16 is connected to the bottle 6 by screw threads. The opening or neck area of bottle 6 seals against pump assembly 16, for example, by way of a screw thread which mates with the pump assembly 16 sealing flange 2c of reservoir 2 between the bottle 6 and the pump assembly 16. Alternatively, or in addition, the collar 8 and the opening or neck area of the reservoir 2 are designed with locking features that permit the override of the pump assembly 16 during assembly but subsequently prevent the unscrewing and disassembly of the pump assembly 16 and the opening of the system. This prevents any unintended contamination by the consumer and also eliminates the possibility of refilling the system.

The pump assembly 16 is thus connected to a valve assembly 3a having an actuator 17, an inner core 10, an axially extending blind passageway 11, ports 12, a flexible membrane 13, a valve cover 14 with a flange 14a, and a soft cover 7 with a controllable outlet orifice 7a (further described below in connection with the descriptions of FIGS. 4A-D). Optionally, the actuator 17 may be connected to or include an atomizer. In operation, the actuator 17 serves to transfer force via a check valve of the pump assembly 16 to draw flowable substance from the reservoir 2, thus providing the force necessary to dispense flowable substance. For example, conventional pumps may be utilized in this manner.

Furthermore, the reservoir 2 can be disposed within a bottle 6 whose open end is sealed by a plug 2c. Plug 2c serves to protect the reservoir 2 from damage, rupture or inadvertent application of force on the reservoir 2.

Figure 3:
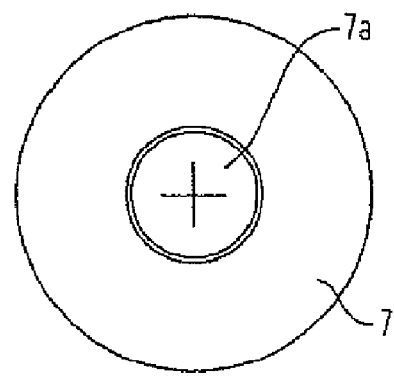
FIG. 3 is an exploded view of the soft cover and its controllable outlet orifice according to an exemplary embodiment of the present invention wherein the controllable outlet orifice is a cross slit.

Referring now to FIG. 3, the controllable outlet orifice 7a includes a cross-slit enabling substantially dripless dispensing of the flowable substance. The cross-slit causes the controllable outlet orifice 7a to self close on itself after pressure is released.

The controllable outlet orifice 7a can be formed as desired to provide a spray or a stream of the flowable substance. Alternatively, by selectively dimensioning the controllable outlet orifice 7a, a drop-like amount of the flowable substance can be dispensed, for example if an eye care solution is being dispensed. If a greater amount of the flowable substance is to be dispensed, the controllable outlet orifice 7a can be formed for dispensing a larger quantity of the flowable substance, for example, an eye or nasal solution and/or gel. In a further alternative, the controllable outlet orifice 7a can be formed with a protruding ring-like structure to reduce the surface tension of the flowable substance when dispensed.

Referring now to FIGS. 4A-D, the valve assembly 3 preferably has an inner core 10, an axially extending blind passageway 11, ports 12, a flexible membrane 13, a valve cover 14 with a flange 14a, and a soft cover 7 with a controllable outlet orifice 7a. An over cap 15 is placed over the valve assembly 3 when it is not in use, protecting it from contact with ambient contaminants.

In the valve assembly 3, an axially extending inner core 10 bears against the opening of the reservoir 2 so that flow from the reservoir enters into an axially extending blind passageway 11 in the inner core. The passageway 11 extends for a major portion of the axial length of the inner core. At approximately half the length of the passageway 11, the inner core has a pair of ports 12 extending transversely of the passageway axis from the surface of the passageway to the outer surface of the inner core 10. The inner core 10 is formed of, for example, a rigid plastic material and terminates inwardly of the outlet end of the valve assembly. Furthermore, in exemplary embodiments, upon assembly and filling of the assembly no air is present inside the passageway 11 and the ports 12. It should be noted that additional ports 12 may be located through the inner core 10.

Furthermore, in exemplary embodiments the inner core 10 and the flexible membrane 13 are constructed such that they fit tightly together, for example having very close tolerances which allow for an air-tight seal to be formed between the flexible membrane 13 and the inner core 10. In further exemplary embodiments the molding process for the flexible membrane 13 and the inner core 10, as well as other components described above as sealing against one another is an asymmetric molding process which creates a surface substantially free of defects or seam lines at the areas of contact where sealing occurs. Accordingly, in an exemplary embodiment, very close tolerances between the parts, for example the inner core 10 and flexible membrane 13 and the other parts, are used to provide an optimal seal and operation of the valve assembly.

A flexible membrane 13, such as an elastomeric member, is fitted tightly over the outer surface of the inner core and extends from the opening in the reservoir 2 to the opposite end of the inner core 10. As can be noted in FIGS. 4A-D, the thickness of the membrane is preferably variable along its axial length. In the region of the outlet end of the inner core has, for example, an axially extending continuous uninterrupted end considerably thicker than the remainder of the flexible membrane 13. That is, the band is not separated in the axial direction by axially extending cuts. The thicker end ensures that after the valve has dispensed fluid, as further described below, the valve closes at the end closest to the opening 7a first, therefore preventing any backflow. This is effected by the heavy wall thickness which provides for greater tension. As a result, the flexible membrane 13 exhibits non-uniform tension.

In a further example, in yet other embodiments, the thickness of the membrane may be variable along its axial length and the region surrounding the outlet end of the inner core has, for example, an axially extending continuous uninterrupted annular band considerably thicker than the remainder of the flexible membrane 13. Furthermore, in certain embodiments, the band is not separated in the axial direction by axially extending cuts. Alternatively, the elasticity or durometer of the end of the flexible membrane closest to the valve opening may be varied, for example it may be reduced, such that the end closest to the valve opening seals first when pressure is relieved.

In a further embodiment, flexible membrane 13 and inner core 10 are substantially tapered or substantially conical at the ends closest to the controllable outlet orifice 7a such that the inner core 10 nest into the flexible membrane 13 one another when being assembled by high speed automated production equipment.

At its end adjacent to the opening of the reservoir 2, the flexible membrane 13 has an outwardly extending flange bearing against a flange on the inner core located at the opening from the reservoir.

An axially extending valve cover 14 encircles the flexible membrane 13 and, as shown in the rest position in FIG. 2a, is spaced radially outwardly from the outer surface of the flexible membrane. The end of the valve cover 14 adjacent the reservoir 2 has a radially outwardly extending flange 14a bearing against the flange at the end of the flexible membrane effecting the seal for the valve assembly at the opening from the reservoir 2.

The valve cover 14 is formed, for example, of an inner layer of an elastomeric material extending axially from its flange 14a to and over the outlet end of the valve assembly 3. Elastomeric material forms a soft cover 7 over the outlet end of the valve cover 14 which is particularly advantageous when the valve assembly is used for dispensing an eye care solution. Such a soft cover 7 prevents, for example, any likelihood of harm to the delicate outer surfaces of the eye or surrounding tissue. The soft cover 7 has a controllable outlet orifice 7a for dispensing the flowable substance. The outlet orifice is closed in the rest position of the continuously sealing one way valve assembly and open in the dispensing position.

Referring yet again to FIGS. 4A-D and to FIG. 5, various embodiments of the valve assembly 3 are depicted having variations in the structure of the soft cover 7 as described below.

Figure 4A:
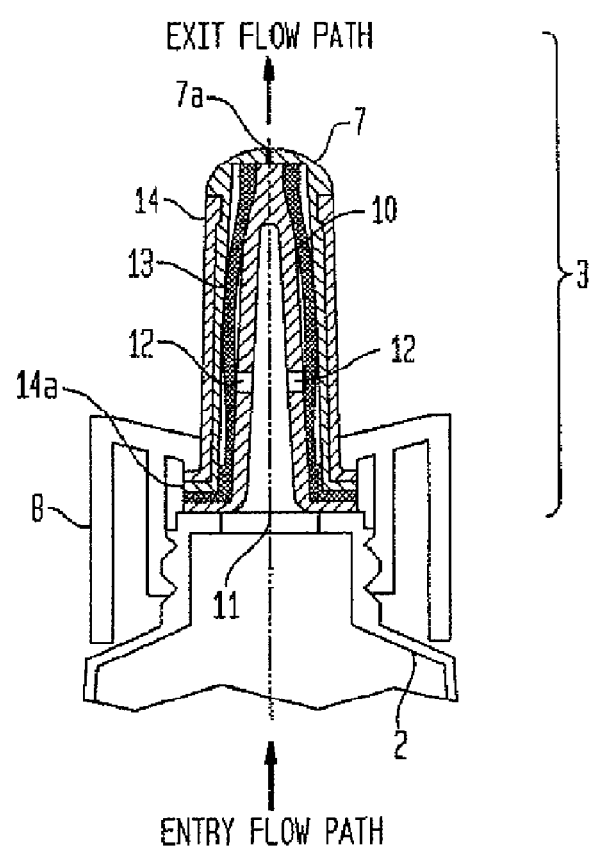
FIG. 4A is an enlarged axially extending partial view of the continuously sealing one way valve assembly with a substantially flat topped soft cover according to an exemplary embodiment of the present invention.

Referring now especially to FIG. 4A, a valve assembly having a flat topped soft cover 7 is provided. The soft cover 7 has a flattened top, which allows for less flowable substance to adhere to the controllable outlet orifice 7a because the flattened top results in a shorter controllable outlet orifice 7a. The soft cover 7 has a controllable outlet orifice 7a which can be formed as desired to provide a spray or a stream of the flowable substance. Furthermore, the controllable outlet orifice 7a can be a cross-slit as shown in FIG. 3. Alternatively, by selectively dimensioning the controllable outlet orifice 7a, a drop-like amount of the flowable substance can be dispensed, for example if an eye care solution or other solution typically delivered in droplet form, is being dispensed. If a greater amount of the flowable substance is to be dispensed, the controllable outlet orifice 7a can be formed for dispensing a larger quantity of the flowable substance, for example by having a larger diameter opening.

Figure 4B:
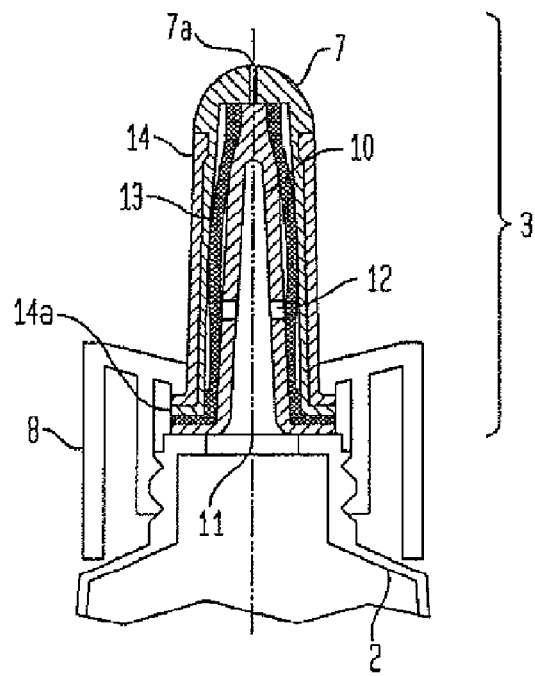
FIG. 4B is an enlarged axially extending partial view of the continuously sealing one way valve assembly with a rounded soft cover according to an exemplary embodiment of the present invention wherein the continuously sealing one way valve assembly is in the rest position.
Figure 4C:
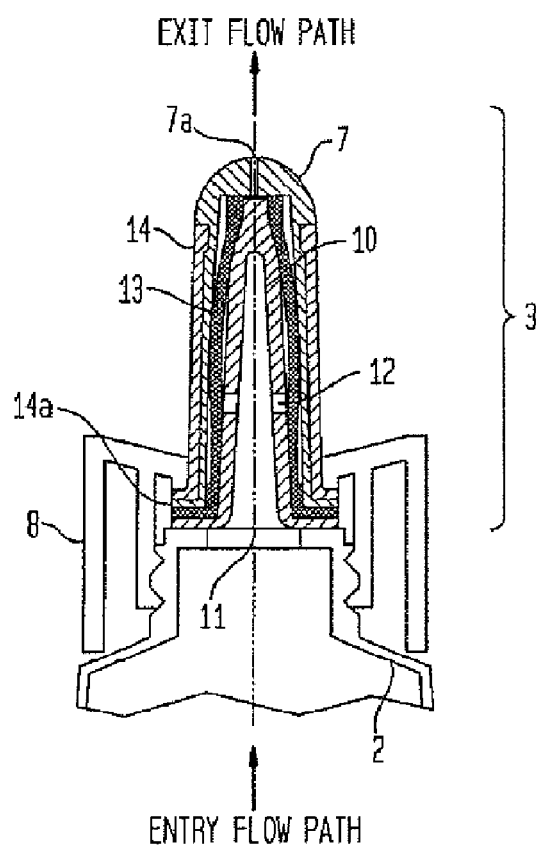
FIG. 4C is an enlarged axially extending partial view of the continuously sealing one way valve assembly with a rounded soft cover according to an exemplary embodiment of the present invention wherein the continuously sealing one way valve assembly is in the dispensing position.

Referring now especially to FIGS. 4B-C, a valve assembly having a rounded soft cover 7 is provided. The soft cover 7 has a rounded top useful for dispensing flowable substance into the outer surfaces of the eye and surrounding tissue or other sensitive body areas. Because the rounded tip lacks sharp edges, damage to the eye or other sensitive tissues is avoided or reduced if incidental contact occurs during administration of the flowable substance. The soft cover 7 has a controllable outlet orifice 7a which can be formed as desired to function with a spray or a stream of the flowable substance. Furthermore, the controllable outlet orifice 7a can be a cross-slit as shown in FIG. 3. Alternatively, by selectively dimensioning the controllable outlet orifice 7a, a drop-like amount of the flowable substance can be dispensed, for example if an eye care solution or other solution typically delivered in droplet form, is being dispensed. If a greater amount of the flowable substance is to be dispensed, the controllable outlet orifice 7*a* can be formed for dispensing a larger quantity of the flowable substance, for example by having a larger diameter opening.

Referring now especially to FIG. 4D, a valve assembly having a flat cover 7 which has an enlarged version of controllable outlet orifice 7*a* is provided. The enlarged version of controllable outlet orifice 7*a* is able to accommodate the inner core 10 and flexible membrane 13 and is suitable for dispensing viscous flowable substances such as lotions, creams and emollients, but may also be used for any flowable substance. The enlarged version of controllable outlet orifice 7*a* allows flowable substance to be dispensed without having to move through two openings—namely the opening at the end of the flexible elastomer 13 and the controllable outlet orifice 7*a*, since these are now flush.

Referring now to FIG. 5 the gap formed between inner core 10 and the flexible membrane 13 by the pressurized fluid flowing out of ports 12 can more easily be seen. The controllable outlet orifice 7*a* in soft cover 7 can also be seen and may for example be a substantially uniform circular bore thought the material of soft cover 7 or may be suitably dimensioned as described in the preceding paragraphs.

Referring now to FIGS. 6A-B, in another embodiment, flowable substance flows through a single port 12 in inner core 10 and expands the flexible membrane 13, swirling around the exterior of inner core 10, and exiting via an outlet port 12*a* as shown in FIGS. 6A and 6B. This results in the need for less cracking pressure to dispense flowable substance and is particularly advantageous for use with, though not limited to, flowable substances having higher viscosities such as lotions, creams and emollients. It should be noted that additional ports 12 may be located through the inner core 10.

In exemplary operation, when the flowable substance is to be dispensed, the over cap 15 is removed and pressure is applied to the actuator 2*a* of the reservoir 2 so that an amount of the flowable substance passes out of the reservoir into the passageway 11 in the inner core 10. The substance flows through the ports 12 and expands the flexible membrane 13 radially outwardly and flows toward the outlet end of the flexible membrane where it exits from the flexible membrane radially inwardly into the controllable outlet orifice 7*a* in the cover and is dispensed.

When the flowable substance is being dispensed and exits the outlet end of the flexible membrane, it flows radially inward to the controllable outlet orifice 7*a* which then opens allowing the substance to flow out of the valve assembly. When the flowable substance is dispensed and pressure on the source is withdrawn the controllable outlet orifice 7*a* closes blocking any backflow into the valve assembly. An over cap 15 is placed over the valve assembly 3 when it is not in use, protecting it from contact with ambient contaminants.

In another embodiment, as depicted in FIGS. 6A and 6B for example, flowable substance flows through a single port 12 in inner core 10 and expands the flexible membrane 13, swirling around the exterior of inner core 10, and exiting via an outlet port 12*a* as shown in FIGS. 6A and 6B. This results in, for example, the need for less cracking pressure to dispense flowable substance and is particularly advantageous for use with, though not limited to, flowable substances having higher viscosities such as creams and emollients.

By releasing the pressure on the actuator 2*a* of the reservoir, the dispensing operation is terminated and the flexible membrane 13 returns inwardly into contact with the outer surface of the inner core 10. The inward movement of the flexible membrane starts at its outlet end because of its increased thickness and affords gradual contact with the outer surface of the inner core, returning any flowable substance through the ports back into the reservoir whereby contaminants cannot enter the reservoir. Dispensing individual portions of the flowable substance can be continued until the reservoir is almost completely emptied. As a result of the structure and operation of the valve assembly, the valve assembly according to an exemplary embodiment of the present invention provides substantially uniform pressure on the valve components via the pressurization of the flowable substance.

In still another exemplary embodiment, for example a spray pump such as that depicted in FIG. 2B, an actuator 17 serves to transfer force to the pump assembly 16 when it is depressed. This in turn compress the reservoir 2, thus providing the force necessary to open the valve assembly and in certain embodiments described above, controllable outlet port 7*a*, to dispense flowable substance.

Referring now to FIGS. 7A-D, in accordance with yet other embodiments of the present invention, a metered drop push button dispenser system which prevents contamination of the reservoir 2 and the interior components which contact flowable substance and which allows for a metered volume of flowable substance to be dispensed is provided. Such a device can be achieved by the use of a button 17 optionally having rounded front tabs, check valve 18, chamber 19 optionally having angled cam flanges on each side, spring 20, piston 21, which may be hollow and optionally have cam flanges, and tip 22 all of which may be contained in at least one housing 23 located in between the reservoir 2 and the outlet of the device (for example, the previously described outlet orifice 7*a*). Alternatively, the housing 23 can also encompass the reservoir 2. The check valve 18 prevents flowable substance from the valve assembly 3 and other components downstream of the reservoir 2 from reversing back into the reservoir 2. In an alternative embodiment, a reservoir 2*b* is provided which is preferably a substantially rigid structure, such as a substantially rigid cylinder or other shape and may optionally contain a tube, bellows, pouch or other similar container for flowable substance, or may itself contain the flowable substance. It is appreciated that the check valve 18 is preferably a disk check valve, though ball, duck bill or other check valve types may be used.

Figure 7A:
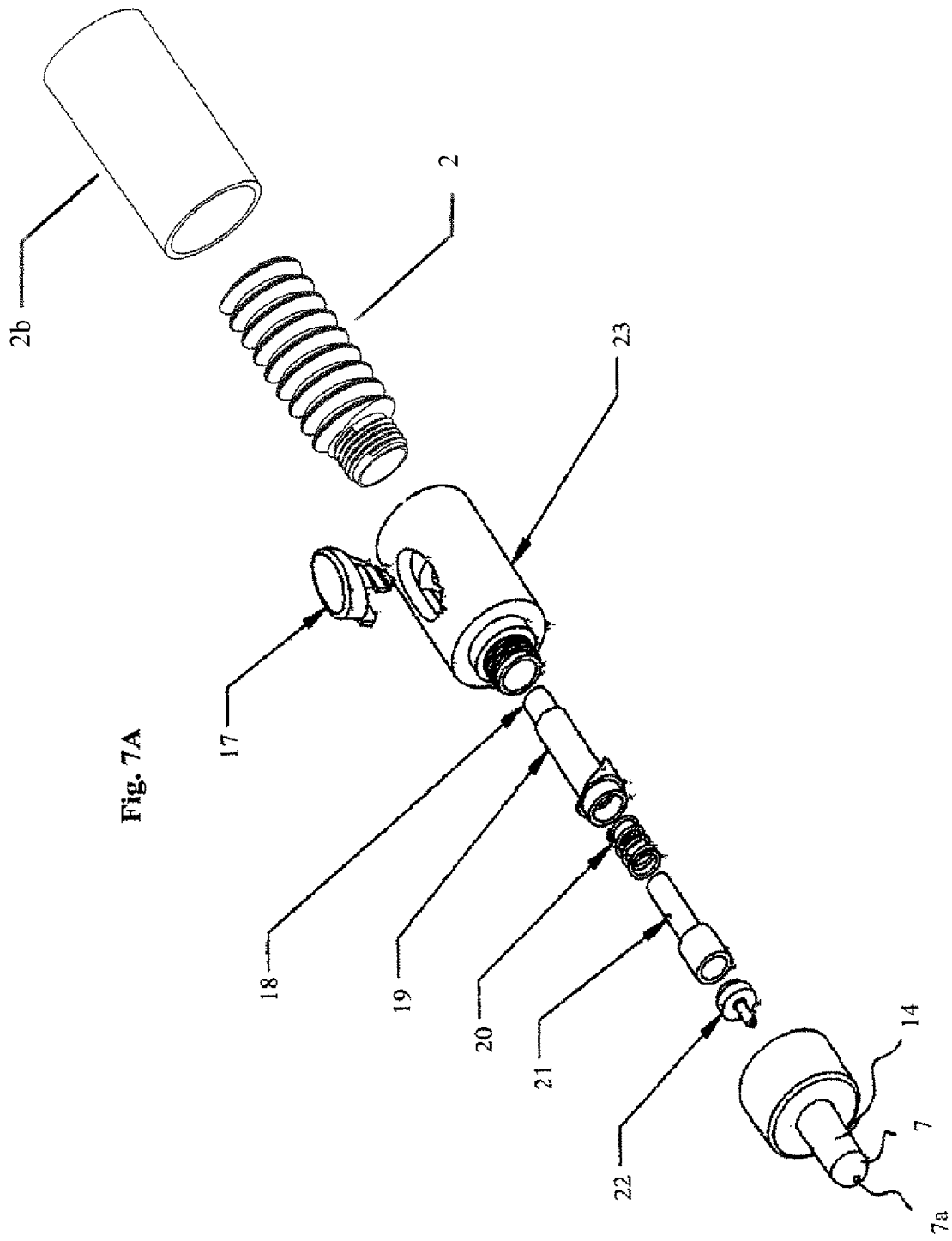
FIG. 7A is an axially extending view of a metered push button dispenser system according to an exemplary embodiment of the present invention.
Figure 7B:
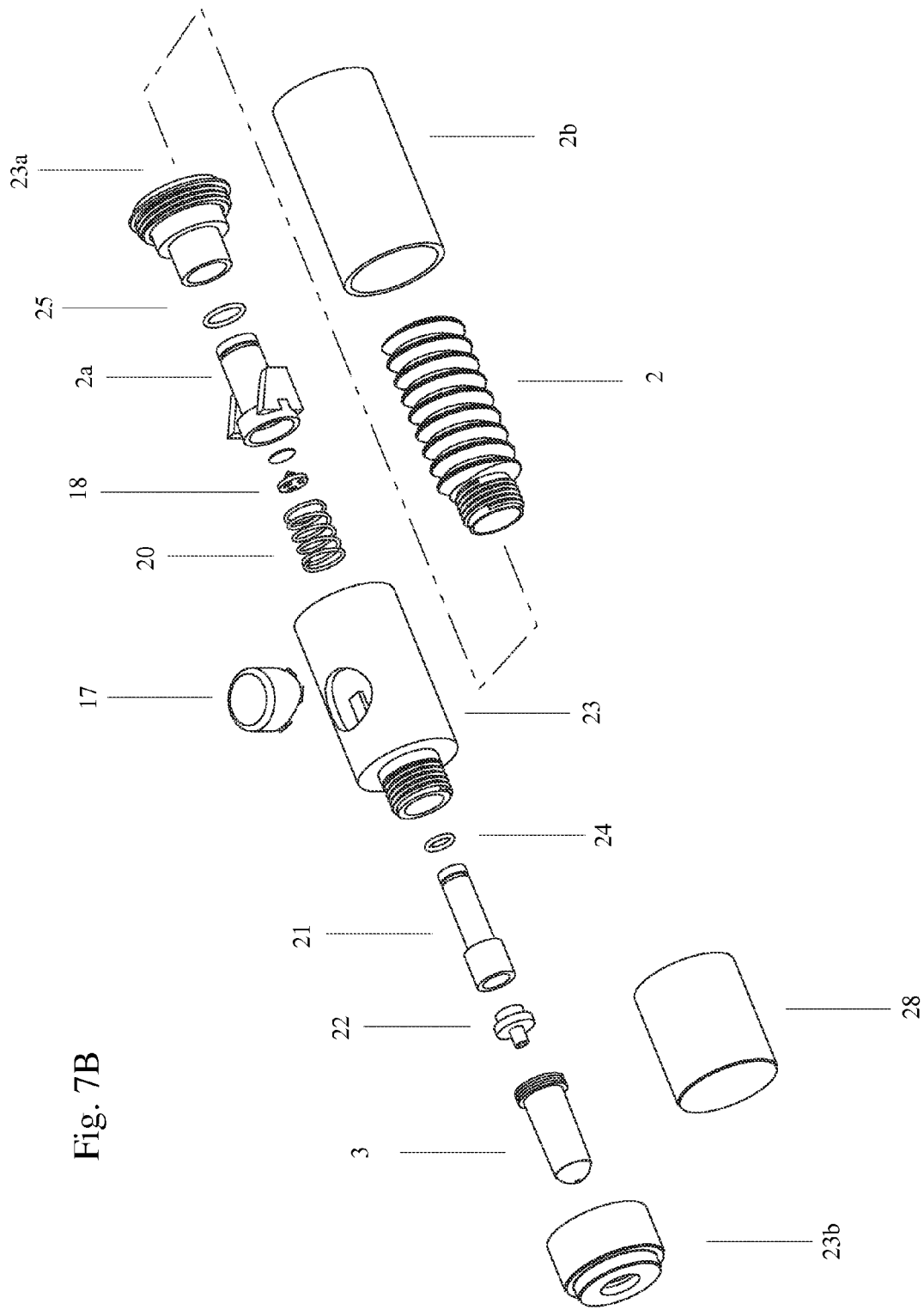
FIG. 7B is an axially extending view of a metered push button dispenser system according to another exemplary embodiment of the present invention.
Figure 7C:
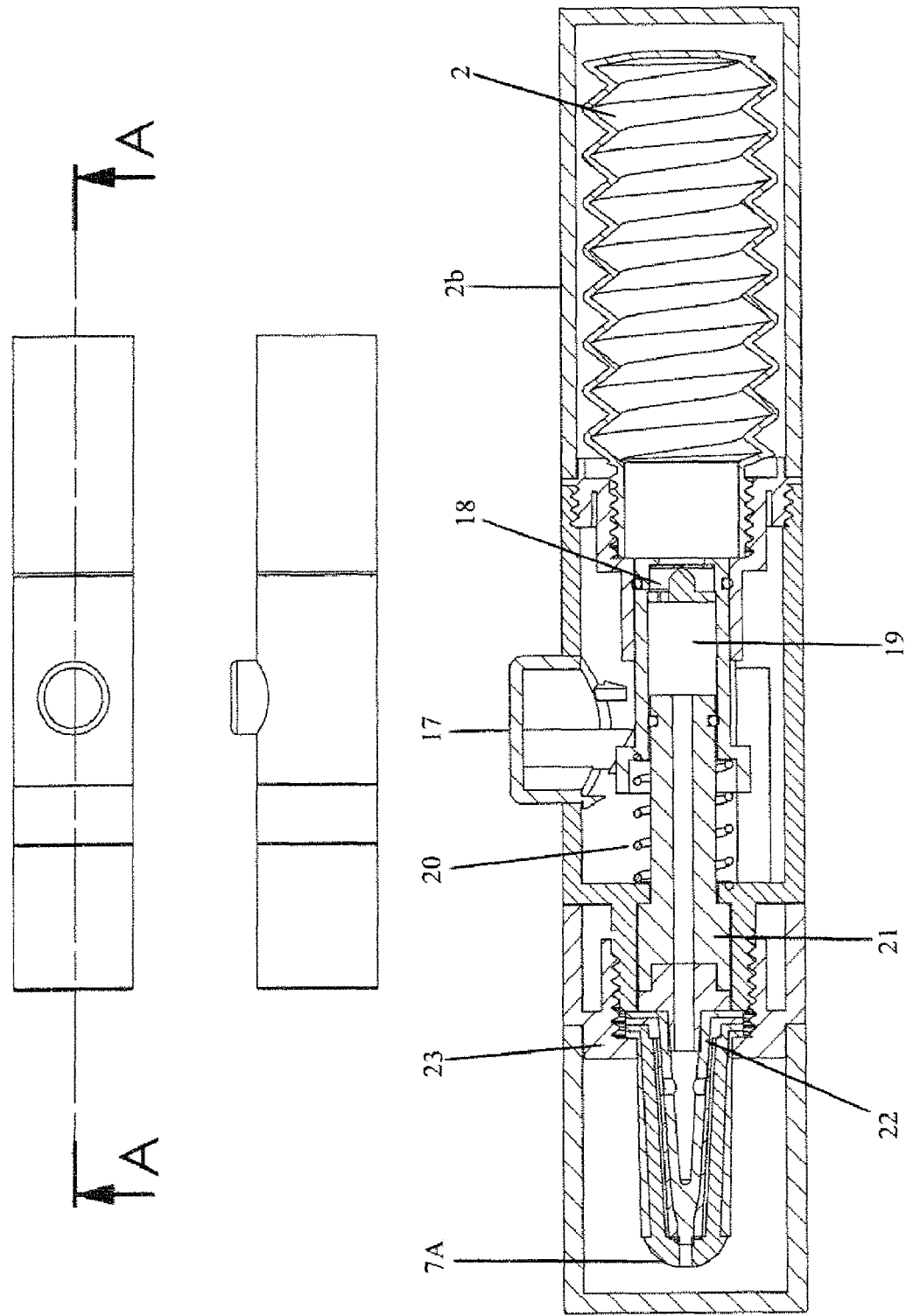
FIG. 7C is a cut away of a metered push button dispenser system according to an exemplary embodiment of the present invention.

Referring now to FIG. 7B, o-rings 24 and 25 seal the piston and chamber to the housing 23 and housing back 23*a*, preventing leakage and entry of solid, gas or liquid contaminants, including, for example, bacteria. Additionally, the button 17 may be encased in a sleeve which is sealed or otherwise attached to the housing 23, preventing leakage and entry of solid, gas or liquid contaminants, including, for example, bacteria. This sleeve can be formed of rubberized or otherwise flexible material so that the button can be depressed from the exterior.

In addition to metered dispensing, the button 17 eliminates the need for user applied pressure on the reservoir itself in order to dispense flowable substance. Elimination of mechanical pressure on the reservoir itself is especially useful in dispensing the contents of partially empty reservoirs which would otherwise require increasing mechanical pressure on the reservoir itself.

Adjustment of the piston 21 and chamber 19 can provide for the dispensing of various volumes of flowable substance. For example, the volume may be varied by changing the size of the chamber 19 or the angle of the cam flange. Variable volume dispensing from the same device can be achieved by varying the stroke of the button, for example by placing stops along the path of the button as it is depressed, thus varying the movement of the piston 21. Adjustment of the spring force and the angle of the cam flanges of the piston 21 provide variation of the force required to depress the button 17. Furthermore, adjustment of the spring force and the angle of the cam flanges of the piston provide variation of the force required to depress the button 17.

The check valve 18 prevents the flowable substance from reversing back into the reservoir 2. As previously described, the reservoir 2 is preferably a rigid structure, such as a rigid cylinder or other shape and may optionally contain a tube, bellows, pouch or other similar container for flowable substance, or may itself contain the flowable substance. A dynamic seal is maintained internally between the piston 21 and chamber 19 which prevents leakage and entry of solid, gas or liquid contaminants, including, for example, bacteria.

Figure 7E:
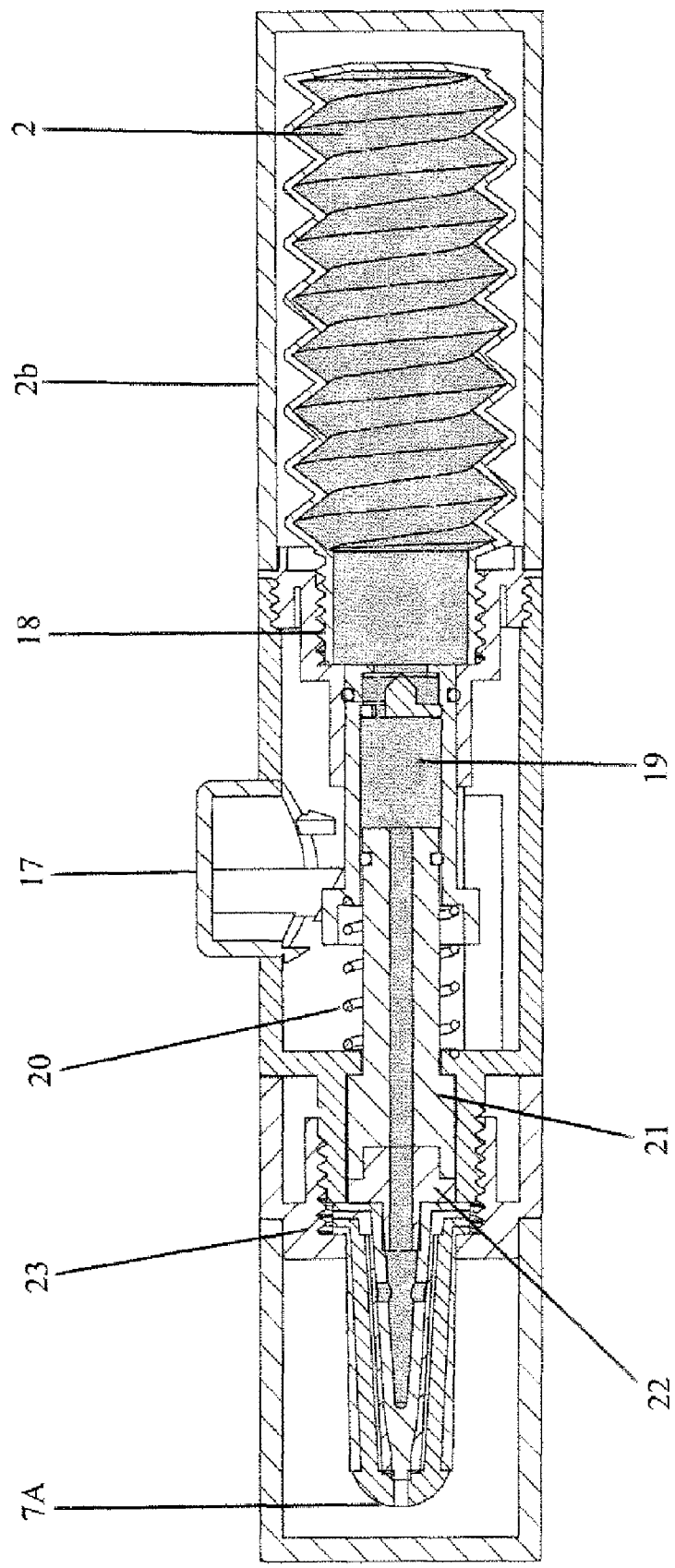
FIG. 7E is a cut away of an exemplary metered push button dispenser system depicting the fluid path during operation of the system.

Referring now to FIG. 7E, flowable substance enters the chamber 19 through a rear port and through the check valve 18. As the button 17 is depressed it pivots down and its rounded front tabs contact the angled cam flange on each side of the chamber 19 forcing it forward against the spring. This forces a measured amount of flowable substance through the hollow piston 21 and out of the tip 22 through the valve assembly 3 and out of the device outlet (for example, the outlet orifice 7a).

Figure 8A:
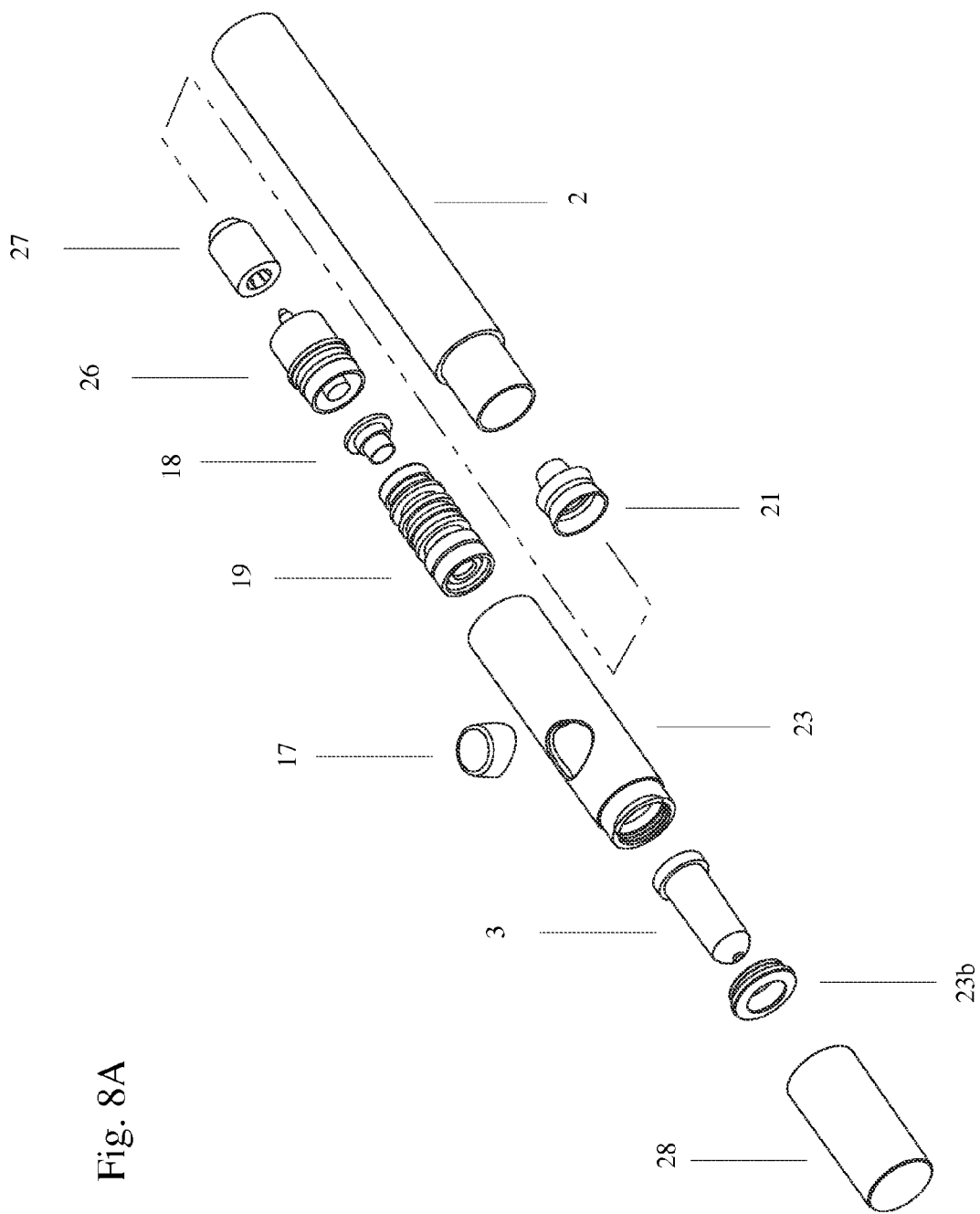
FIG. 8A depicts a metered push button dispenser system according to an exemplary embodiment of the present invention.

Referring now to FIGS. 8A and 8B, in accordance with yet other embodiments of the present invention, a metered drop push button dispenser system which prevents contamination of the reservoir 2b and the interior components which contact flowable substance and which allows for a metered volume of flowable substance to be dispensed is provided. Such a device can be achieved by the use of a button 17 optionally having rounded front tabs, compressible chamber 19a optionally having angled cam flanges on each side and having a tip sealable with the valve assembly 3, check valve 18, check valve housing 26 and check valve back 27 and tip 22 all of which may be contained in at least one housing 23 located in between the reservoir 2b and the outlet of the device (for example, the previously described outlet orifice 7a) and travelling piston 21a located within reservoir 2b which is preferably a substantially rigid cylinder or other shape and which allows travelling piston 21a to move while maintaining a seal against reservoir 2b. It is appreciated that the valve assembly 3 can be sealed to the housing 23 by use of a mating valve nut 23b forming a threaded or other suitable closure with the housing 23 and that o-rings or other suitable means can be used to further effect the seal. It is further appreciated that the check valve 18 is preferably a disk check valve, though ball, duck bill or other check valve types may be used.

Alternatively, in yet another embodiment, the reservoir 2b can be a substantially rigid structure, such as a substantially rigid cylinder or other shape and may optionally contain a tube, bellows, pouch or other similar container for flowable substance, or may itself contain the flowable substance, in which case the need for a travelling piston 21a is eliminated. In yet another exemplary embodiment, the end opposite the opening in the reservoir 2b can be fitted with a 0.05 to 0.45 micron filter, or preferably a 0.2 micron filter, which prevents the entry of bacteria and other contaminants into the section of the reservoir below the travelling piston as air enters the space created by the forwards movement of the travelling piston 21a, thus providing an additional layer of protection from the entry of bacteria and other contaminants.

Additionally, the button 17 may be encased in a sleeve which is sealed or otherwise attached to the housing 23 preventing leakage and entry of solid, gas or liquid contaminants, including, for example, bacteria. This sleeve can be formed of rubberized or otherwise flexible material so that the button can be depressed from the exterior.

Adjustment of the piston 21 and compressible chamber 19a can provide for the dispensing of various volumes of flowable substance. For example, the volume may be varied by changing the size of the compressible chamber 19a. Variable volume dispensing from the same device can be achieved by varying the stroke of the button, for example by placing stops along the path of the button as it is depressed, thus varying the compression of the compressible chamber 19a.

Figure 8C:
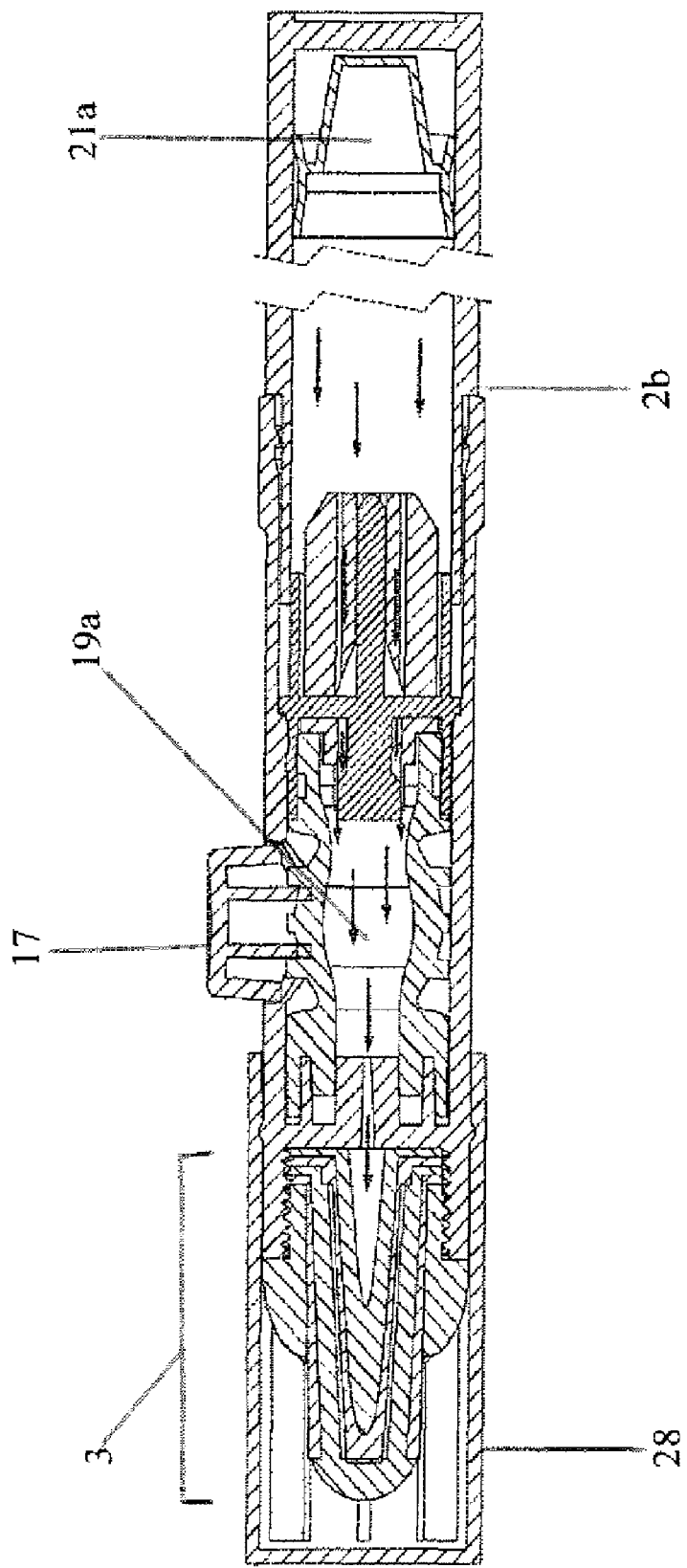
FIG. 8C is a cut away of an exemplary metered push button dispenser system depicting the fluid path during operation of the system.

Referring now to FIG. 8C, upon depressing button 17, the chamber 19 is compressed, increasing the pressure on the flowable substance contained therein and causing it to be expelled through the valve assembly 3 and dispensed. The check valve 18 prevents back flow of the flowable substance from the valve assembly 3 into the reservoir 2b. When the button 17 is released, the expansion of the chamber draws flowable substance from the reservoir 2b, through the check valve 18, thus refilling the compressible chamber 19a and pulling the travelling piston 21a upwards along the reservoir 2b. The strength of the sealing within the valve assembly 3 prevents backflow of air and contaminants into the device when the pressure on the compressible chamber 19a is released.

Figure 9A:
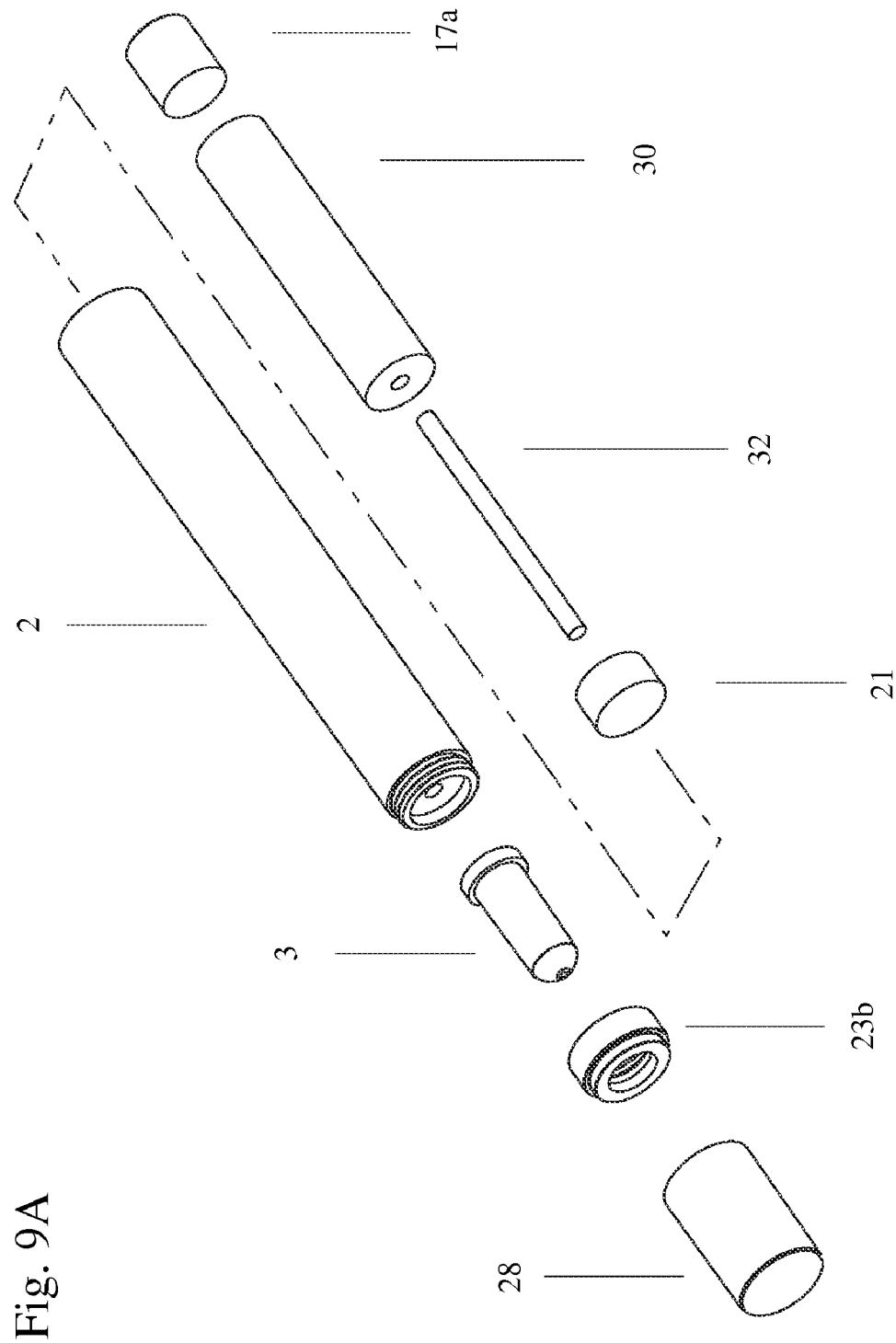
FIG. 9A depicts a metered push button dispenser system according to an exemplary embodiment of the present invention.
Figure 9B:
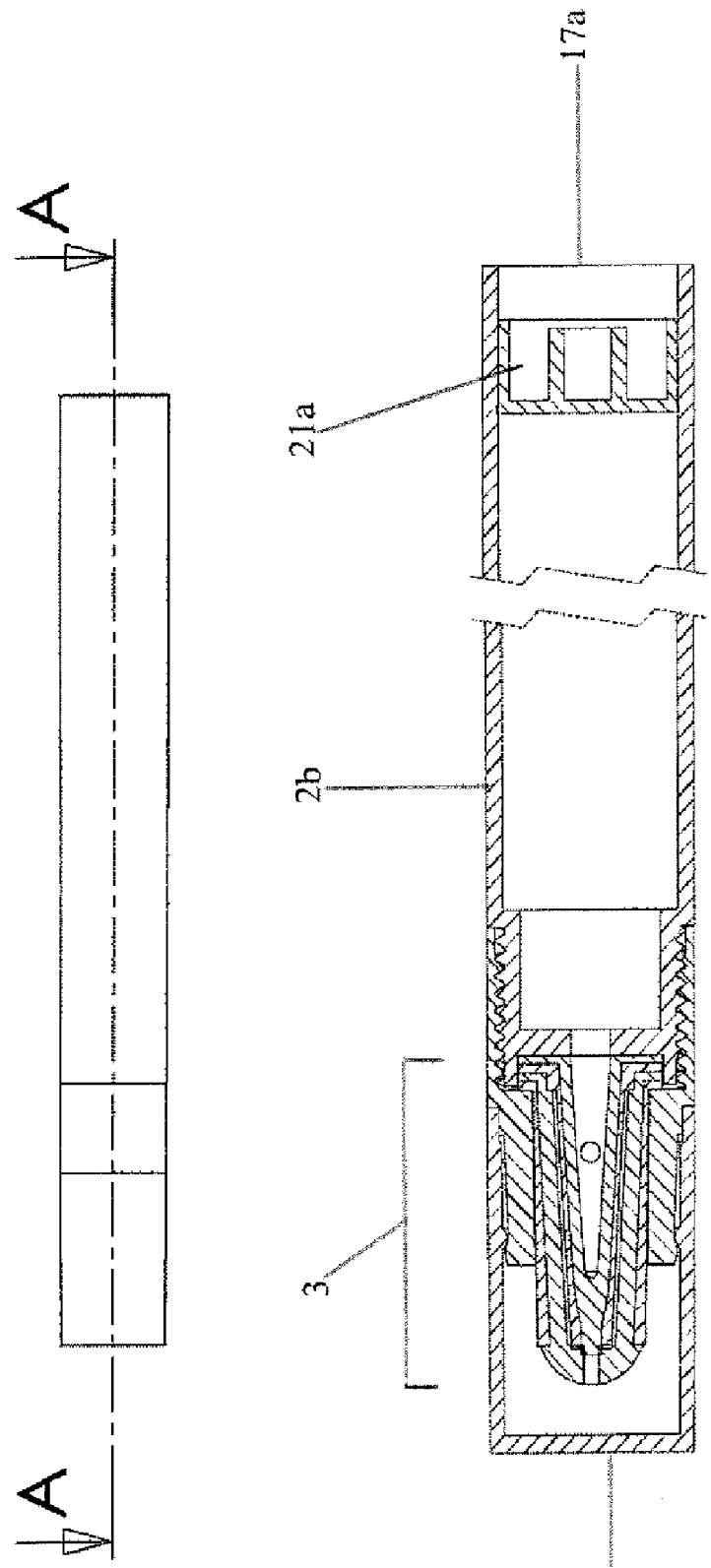
FIG. 9B is an axially extending view of a metered push button dispenser system according to an exemplary embodiment of the present invention.
Figure 9C:
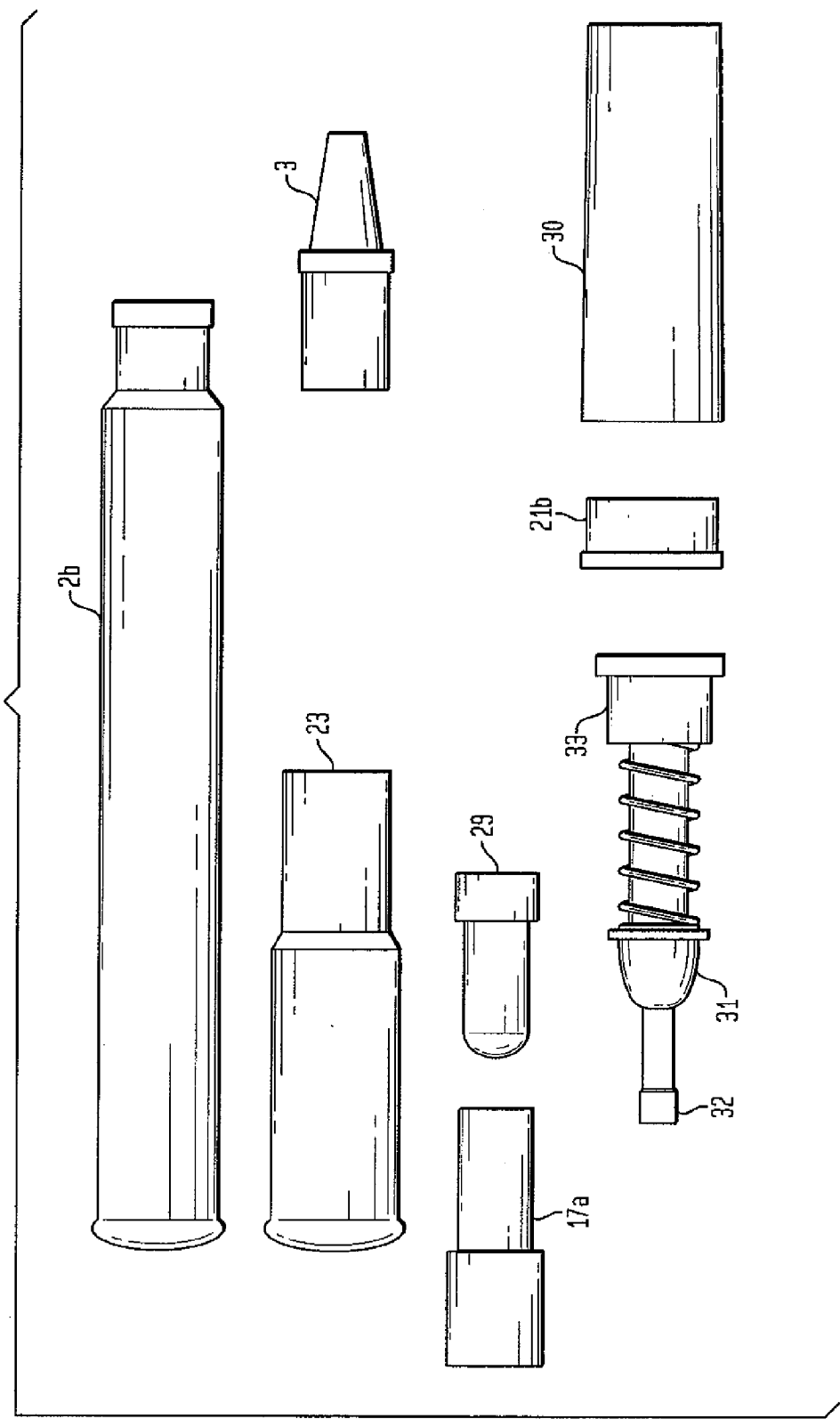
FIG. 9C is a cut away of an exemplary metered push button dispenser system depicting the fluid path during operation of the system.

Referring now to FIGS. 9A-9C, in accordance with still other embodiments of the present invention, a further metered drop push button dispenser system which prevents contamination of the reservoir 2b and interior of the system and which allows for a metered volume of flowable substance to be dispensed is provided. Such a device can be achieved by the use of a rear button 17a and its related components (described below), check valve 18 having a tip sealable with the valve assembly 3, all of which may be contained in at least one housing 23 located in between the reservoir 2b and the outlet of the device (for example, the previously described outlet orifice 7a) and travelling piston 21a located within reservoir 2b which is preferably a rigid tube and which allows travelling piston 21a to move while maintaining a seal against reservoir 2b. It is appreciated that the housing 23 can serve to seal valve assembly 3 and check valve 18 to the reservoir 2b by acting as a valve nut or other suitable closure and that o-rings or other suitable means can be used to further effect the seal. It is further appreciated that the check valve 18 is preferably a disk check valve, though ball, duck bill or other check valve types may be used.

Rear button 17a is connected to a generally cylindrical drive component 29 which is constrained by longitudinal mating ribs within an outer sleeve 30. The outer sleeve 30 is press affixed within the reservoir 2b. A series of mating ramped features occur between the peripheral base edge of the drive component 29 and a rotatable bushing 31. The rotatable bushing is held by mating ribs within the outer sleeve 30. The bushing has internal threads mating with a threaded shaft 32 passing through the center axis of the bushing. The threaded shaft also passes through a threaded collar 33 which is affixed within the outer sleeve 30. The amount of flowable substance dispensed can be modified by varying the linear stroke of the button 17a and drive component 29, angulation and number of beveled ramp features and/or pitch of the threaded shaft 32.

Figure 9D:
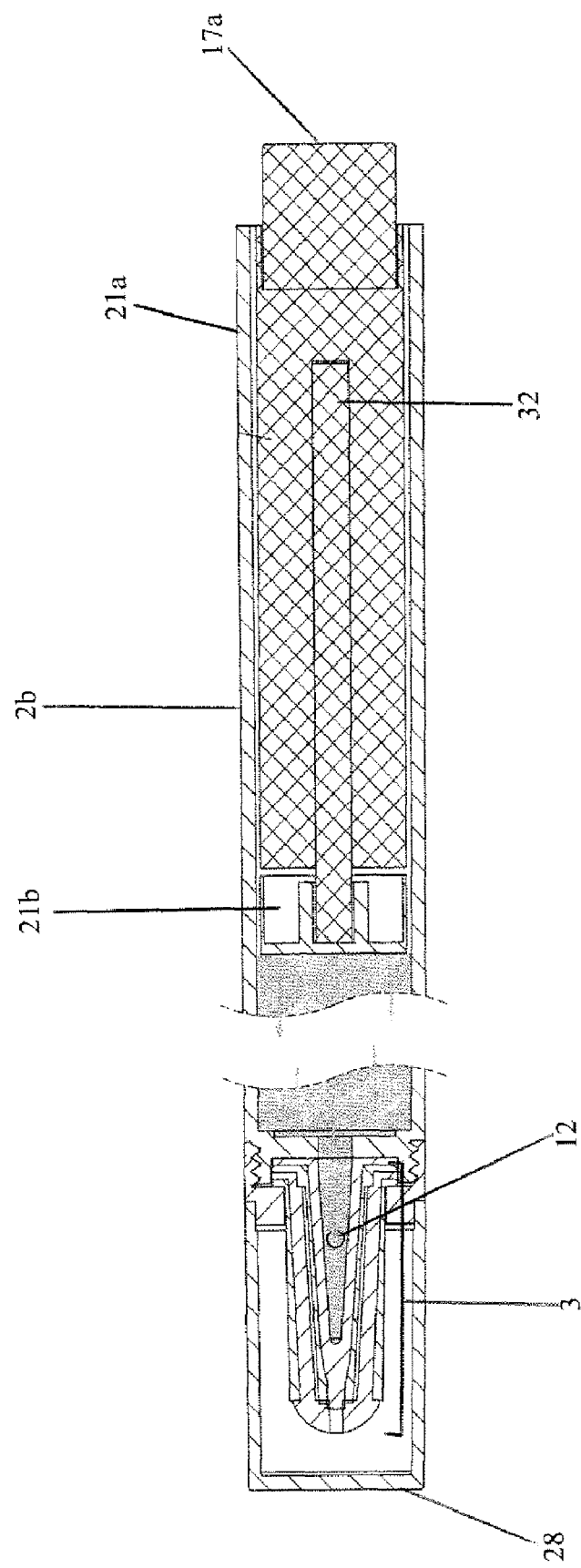
FIG. 9D depicts another axially extending view of the metered dispensing system of FIGS. 9A-9C, showing a proximal portion thereof.

Referring now to FIGS. 9C and 9D, depressing rear button 17a pushes down upon a generally cylindrical drive component 29 which is constrained by longitudinal mating ribs within an outer sleeve 30 to maintain the drive component's linear motion. A series of mating ramped features between the peripheral base edge of the drive component and a rotatable bushing 31 cause the linear motion of the drive component to rotate the bushing. The rotating bushing is constrained linearly with mating ribs within the outer sleeve 30. Rotation of the bushing 31 translates the rotational movement of the bushing 31, through the mating threads, into linear movement of the threaded shaft 29, incrementally advancing the threaded shaft 29 forward. The forward advancing threaded shaft 29 pushes a travelling piston 21b forward ahead of the threaded shaft within the reservoir 2b, causing a predetermined volume to be expelled through the valve assembly 3 and dispensed. A check valve 18 ensures only forward flow of the flowable substance out to the valve assembly 3.

Referring now generally to FIGS. 7A-9C, a cap or overcap 28 may be placed over the portions of the system, for example portions of the valve assembly 3, which protrude from the reservoir 2b, or which protrude from the housing 23 or the housing 23 and valve nut 23a. Referring yet again to FIGS. 7A-9C, as described above, such metered drop push button dispensers can be combined with the valve assembly 3 in one embodiment, or alternatively be provided without the valve assembly 3.

Figure 10A:
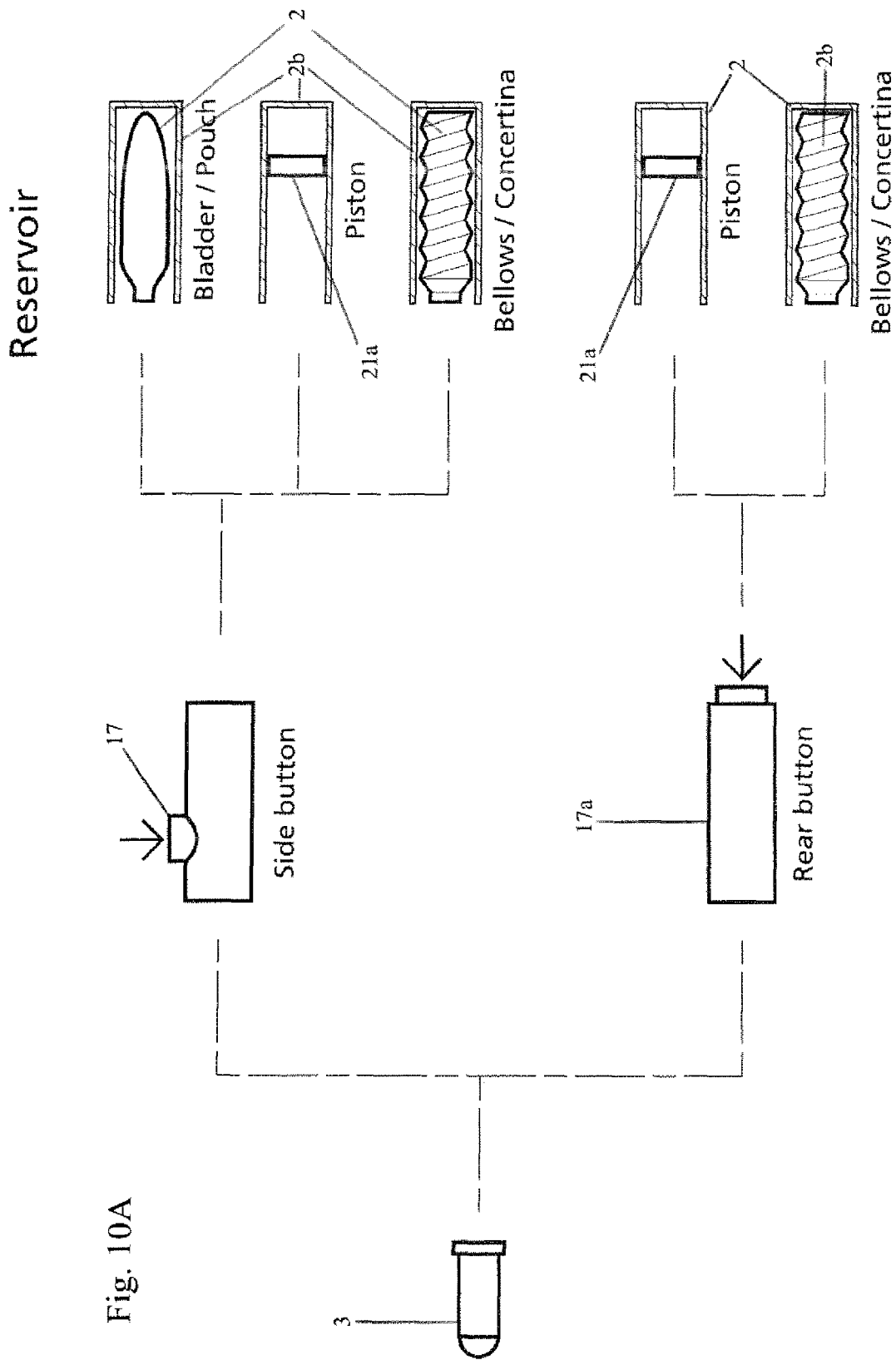
FIG. 10A depicts metered push button delivery or dispensing systems with rigid reservoirs according to exemplary embodiments of the present invention.

Referring now to FIGS. 10A and 10B, exemplary embodiments of substantially rigid reservoirs suitable for holding flowable substance or for holding collapsible reservoirs of the embodiments of the present invention are provided. Such reservoirs are substantially rigid such that force sufficient to defeat the seal of a check valve, e.g. check valve 18 of FIGS. 1-9D and a valve assembly, e.g. valve assembly 3 of FIGS. 1-9D cannot be easily applied to the flowable substance by deformation of the reservoir 2b by way of excessive squeezing or other physical pressure on the reservoir 2b. Such substantial rigidity serves to deter the accidental or intended dispensing of amounts in excess of the premeasured amounts delivered by the dispensing or delivery system.

Elastomers suitable to form the soft cover 7, the flexible membrane 13 and the valve cover 14 in exemplary embodiments of the present invention include thermoplastic elastomers such as Dynaflex manufactured by GLS Corp., C-Flex manufactured by CPT Inc., or Santoprene manufactured by Advanced Elastomer Systems, Inc. The elastomers, and the materials comprising any of the other components of the device may have integrated, impregnated, otherwise placed within them anti-microbial ingredients such as silver ions contained within a ceramic carrier, such as those supplied by AgION, or sustained-release ionic silver compounds, such as those supplied by Westlake Plastic Technologies which are known to be used in the making of anti-microbial plastics. Furthermore, other anti-microbial suitable for compounding with or coating plastics may be used. Furthermore, the soft cover 7 or the flexible membrane 13 or both could, for example, be positively charged to repel residual flowable substance, coated in for example, Teflon type-plastics, have increased surface tension or be anti-wetting, or any combination of the above so as to repel flowable substance.

In further exemplary embodiments, one or more of the button 17, check valve 18, chamber 19, spring 20, piston 21, traveling piston 21b, tip 22 and housing 23 may be formed from hydrophobic or antimicrobial material or be coated with a hydrophobic or anti-microbial coating. For example, components of the device can have integrated, impregnated, coated or otherwise placed within them anti-microbial ingredients such as silver ions contained within a ceramic carrier, such as those supplied by Agion, or sustained-release ionic silver compounds, such as those supplied by Westlake Plastic Technologies which are known to be used in the making of anti-microbial plastics. Furthermore, other anti-microbial suitable for compounding with or coating plastics can be used. Still further, components of the device can for example, be positively charged to repel residual flowable substance, coated in for example, Teflon type-plastics, have increased surface tension or be anti-wetting, or any combination of the above so as to repel flowable substance. Even further, one or more, or all, components of the valve assembly, actuator assembly and source can have integrated, impregnated, coated, or otherwise placed within them anti-microbial ingredients or water repellant ingredients.

In yet other exemplary embodiments, including those described above, the durometer of the elastomers can be varied in relation to the viscosity of the flowable substance. For example, assemblies containing substances with comparatively higher viscosities would utilize softer, i.e. lower durometer elastomers, in order to reduce the cracking force needed to dispense flowable substance, whereas lower viscosity flowable substances would utilized harder, i.e. higher durometer elastomers to maintain a strong seal. Likewise, flowable substances containing lubricants would also utilize harder, i.e. higher durometer elastomers to maintain a strong seal.

As described above, the parts of the dispending and delivery device, including the valve assembly may be manufactured to close tolerances such that they form airtight seals and are close fitting ensuring optimal seals and operation of the device.

A variety of pharmaceuticals, cosmetics, food stuffs and other flowable materials can be dispensed where it is important to maintain them free of contaminants from the ambient atmosphere. The flowable characteristics of the material being dispensed determines or at least may affect the type and dimension of the valve assembly.

According to exemplary embodiments of the present invention, the material forming the controllable outlet orifice 7a does not absorb the flowable substance. As a result, any substance entering the outlet orifice 7 is ejected from the dispenser and does not return into the space between the inner core and the flexible membrane, thereby maintaining the purity or sterility of the product remaining in the reservoir.

It should be understood that the various embodiments of the valve assembly described above can each be used in the various embodiments of the continuously sealing one way valve assembly device.

As mentioned, the flowable substance may be a pharmaceutical cosmeceutical, or nutraceautical, an eye care solution, other opthalmological product, otorhinolarygology product, dermatological product, gynecological product, or product for treating or preventing anorectal, dermatological or pulmonary disorders or any formulation administered to the body through the mucus membranes; a food stuff, such as dairy products, beverages or juices; a cosmetic, such as a skin care solution or toiletries; and liquid vitamins, all of which are intended to be maintained free of contaminants from the ambient atmosphere and of preservatives during storage within the reservoir 2.

According to exemplary embodiments of the present invention, many existing commercial products that contain preservatives can be reformulated into preservative free versions and provided for multiple dose dispensing with the valve assembly and delivery system of the present invention. For example, conventional creams, emollients, eye drops, nasal sprays, cosmetic creams that currently require preservatives, notably parabens and benzalkonium chloride that have proved to be deleterious to tissue, may be reformulated in a preservative free form and are amenable to storage and dispensing from a multidose metered delivery system having the continuously sealing one way valve assembly of the present invention. This can be accomplished by, for example, formulating the product according to its original formulation, but without the preservative, or by readjusting the formulation of the product, for example by changing the excipients or the amount of the excipients or both. Thus, these preservative free products are amenable to storage and dispensing from a multidose metered delivery system having the continuously sealing one way valve assembly of the present invention because they are preservative free formulations.

The following examples provide embodiments describing categories of medical products which are amenable to storage and dispensing from a multidose metered delivery system having the continuously sealing one way valve assembly of the present invention. Preservative-free storage and delivery of formulations also can be accomplished by providing, for example, multi-dose metered, high barrier and for preservative-free systems as described in U.S. Pat. No. RE 34,243, incorporated by reference above and U.S. Pat. Nos. 5,092,855; 5,305,783; 5,279,447; 5,305,786; and 5,353,961 all of which are hereby incorporated by reference in their entirety.

EXAMPLES

Example 1

In an exemplary embodiment, preservative free opthalmological products are amenable to storage and dispensing from a multidose metered delivery system having the continuously sealing one way valve assembly of the present invention. For example, eye drops, and preferably those eye drops involved in chronic care, for example, dry eye, glaucoma, allergies and NSAIDs, and also those eye drops intended for acute care, for example during ocular surgery, are amenable to storage and dispensing from a multidose metered delivery system having the continuously sealing one way valve assembly of the present invention. As a further example, those eye drops used to relieve eye fatigue, those eye drops used to relieve dry eye, those eye drops used relieve dry eye due to computer use, television use, or fatigue due to prolonged awake periods are amenable to storage and dispensing from a multidose metered delivery system having the continuously sealing one way valve assembly of the present invention.

Examples of dry eye products can include dry eye products comprising methycellulose, hyaluronic acid, polyethelene glycol 400 0.4%, propylene glycol 0.3%, glycerin, and mineral oils. Examples of glaucoma products include glaucoma products comprising timolol 0.25%/0.50%, brimonidine tartrate 0.1%, bimatoprost 0.03% and travaprost 0.004%. Examples of allergy products include allergy products comprising olopatadine HCL 0.1% and predisalone acetate 1%. Examples of NSAID products include NSAID products comprising ketorolac 0.5% and diclofenac 0.1%.

Example 2

In an exemplary embodiment, preservative-free otorhinolarygological products are amenable to storage and dispensing from a multidose metered delivery system having the continuously sealing one way valve assembly of the present invention. For example, nasalia medicines, and preferably nasal sprays, external ear creams, ear drops, steroid ear drops, antibiotic ear drops, nose drops, and nose drops comprising phenylephrine 0.25% and pseudoephedrine 30 mg, are amenable to storage and dispensing from a multidose metered delivery system having the continuously sealing one way valve assembly of the present invention.

Example 3

In an exemplary embodiment, preservative free dermatological products are amenable to storage and dispensing from a multidose metered delivery system having the continuously sealing one way valve assembly of the present invention. For example, preservative free skin preparations; scalp preparations; corticosteroid creams, lotions and ointments; topical antibiotics and topical anti-fungal agents are amenable to storage and dispensing from a multidose metered delivery system having the continuously sealing one way valve assembly of the present invention. Thus, these preservative free dermatological products are amenable to storage and dispensing from a multidose metered delivery system having the continuously sealing one way valve assembly of the present invention because they are preservative free formulations.

Example 4

In an exemplary embodiment, preservative free products for the treatment or prevention of dermatologic disorders are amenable to storage and dispensing from a multidose metered delivery system having the continuously sealing one way valve assembly of the present invention. For example, preservative free skin preparations; scalp preparations; corticosteroid creams, lotions and ointments; topical antibiotics; topical anti-fungal agents; therapeutic skin creams including anti-bacterial, anti-fungal/parasitic, allergic and non-specific dermatitis creams and emollients and all cosmetic dermatologic compounds used for dermatologic disorders are amenable to storage and dispensing from a multidose metered delivery system having the continuously sealing one way valve assembly of the present invention.

Example 5

In an exemplary embodiment, products for the treatment or prevention of anorectal disorders are amenable to storage and dispensing from a multidose metered delivery system having the continuously sealing one way valve assembly of the present invention. For example, preservative free creams, topical anaesthetics, lubricating jellies and jelly or other preparations for hemorrhoid treatment, prevention or management, are amenable to storage and dispensing from a multidose metered delivery system having the continuously sealing one way valve assembly of the present invention.

Example 6

In an exemplary embodiment, preservative free products for the treatment or prevention of pulmonary disorders are amenable to storage and dispensing from a multidose metered delivery system having the continuously sealing one way valve assembly of the present invention. For example preservative free formulations of products for chronic obstruction disorder, for example, aerosol nebulizers using B-adrenergic, anticholinergic, corticosteroid and theophyline derivatives requiring multi-dose application are amenable to storage and dispensing from a multidose metered delivery system having the continuously sealing one way valve assembly of the present invention.

Example 7

In an exemplary embodiment, preservative free gynecological products are amenable to storage and dispensing from a multidose metered delivery system having the continuously sealing one way valve assembly of the present invention. For example, vulvovaginal treatment medicines, such as medicines for contact irritant or allergic vulvitis, chemical irritation, bacterial vaginosis, Candidal vaginitis therapy including all azoles and nystatins, butoconazole, butoconalzole 2%, clotrimazole, clotrimazole 1%, metronidazole and trichomonas treatments are amenable to storage and dispensing from a multidose metered delivery system having the continuously sealing one way valve assembly of the present invention.

Example 8

In an exemplary embodiment, preservative free lens care products are amenable to storage and dispensing from a multidose metered delivery system having the continuously sealing one way valve assembly described herein. For example, contact lens rinsing, cleaning disinfecting and storage solutions, or a multi-purpose solution encompassing contact lens rinsing, cleaning disinfecting and storage are amenable to storage and dispensing from a multidose metered delivery system having the continuously sealing one way valve assembly of the present invention.

Example 9

In an exemplary embodiment, preservative free eye wash products (e.g. irrigation solutions) are amenable to storage and dispensing from a multidose metered delivery system having the continuously sealing one way valve assembly described herein. For example, eye wash products used to clear the eye of environmental contamination are amenable to storage and dispensing from a multidose metered delivery system having the continuously sealing one way valve assembly described herein. As a further example, eye wash products used to clear the eye of environmental contamination such as pollen or dirt are amenable to storage and dispensing from a multidose metered delivery system having the continuously sealing one way valve assembly of the present invention.

Although the system is designed for use with various preservative free formulations it may also be used with formulations which are not preservative free.

The invention claimed is:

1. A continuously sealing one way valve assembly and delivery system for dispensing a flowable substance, comprising:
    a source for storage of the flowable substance, the source having an opening;
    an actuator assembly coupled to the opening of the source and
    a valve assembly coupled to the actuator assembly, said valve assembly including
        (i) an inner core having an inlet opening for receiving the flowable substance into a passageway and at least one port opening from the passageway,
        (ii) a hollow flexible membrane having a first end and a second end, the first end being thicker than the second end, wherein the hollow flexible membrane is fitted over an outer surface of the inner core and when the flowable substance is placed under pressure the flowable substance exits through the at least one port opening and expands said membrane outwardly from said outer surface of said inner core; and
        (iii) a cover enclosing the flexible membrane and having an outlet orifice for dispensing the flowable substance from the valve assembly when pressure is applied to the flowable substance;
    wherein when the pressure on the flowable substance is released, the first end of the hollow flexible membrane moves back into tightly fitting contact with the outer surface of the inner core before the remainder of the hollow flexible membrane moves back into tightly fitting contact with the outer surface of said inner core.

2. The valve assembly and delivery system as set forth in claim 1 wherein the actuator assembly includes a chamber coupled to a button and a check valve.

3. The valve assembly and delivery system as set forth in claim 1 wherein a chamber coupled to a button and a check valve are each located upstream from the source and wherein the check valve is actuated by the button such that flowable substance enters the chamber, resulting in the delivery of a premeasured amount of flowable substance from a reservoir.

4. The valve assembly and delivery system as set forth in claim 1 wherein the actuator assembly includes a piston.

5. The valve assembly and delivery system as set forth in claim 1 wherein the hollow flexible membrane has an axially extending uninterrupted continuous band at the first end of the hollow flexible membrane adjacent the outlet orifice in the cover and completely encircling the core.

6. The valve assembly and delivery system as set forth in claim 1, wherein the valve assembly, actuator assembly and source are coupled in fluid tight contact with each other.

7. The valve assembly and delivery system of claim 1, wherein the source is filled with a preservative free product.

8. The valve assembly and delivery system as set forth in claim 1, wherein the continuously sealing one way valve assembly and delivery system can dispense multiple doses of preservative-free product.

9. A continuously sealing one way valve assembly and delivery system for dispensing a flowable substance, comprising:
    a source for storage of the flowable substance, the source having an opening;
    an actuator assembly coupled to the opening of the source and
    a valve assembly coupled to the actuator assembly, said valve assembly including
        (i) an inner core having an inlet opening for receiving the flowable substance into a passageway and at least one port opening from the passageway,
        (ii) a hollow flexible membrane having a first end and a second end, the first end being thicker than the second end, wherein the hollow flexible membrane is fitted over an outer surface of the inner core and when the flowable substance is placed under pressure the flowable substance exits through the at least one port opening and expands said membrane outwardly from said outer surface of said inner core; and
        (iii) a cover enclosing the flexible membrane and having an outlet orifice for dispensing the flowable substance from the valve assembly when pressure is applied to the flowable substance;
    wherein when the pressure on the flowable substance is released, the first end of the hollow flexible membrane moves back into tightly fitting contact with the outer surface of the inner core before the remainder of the hollow flexible membrane moves back into tightly fitting contact with the outer surface of said inner core, and
    wherein the actuator assembly comprises a compressible chamber.

10. The valve assembly and delivery system as set forth in claim 9 wherein the actuator assembly includes a chamber coupled to a button and a check valve.

11. The valve assembly and delivery system as set forth in claim 9 wherein a chamber coupled to a button and a check valve are each located upstream from the source and wherein the check valve is actuated by the button such that flowable substance exits the chamber, resulting in the delivery of a premeasured amount of flowable substance from the source.

12. The valve assembly and delivery system as set forth in claim 9 wherein the hollow flexible membrane has an axially extending uninterrupted continuous band at the first end of the hollow flexible membrane adjacent the outlet orifice in the cover and completely encircling the core.

13. The valve assembly and delivery system as set forth in claim 9, wherein the valve assembly, actuator assembly and source are coupled in fluid tight contact with each other.

14. A continuously sealing one way valve assembly and delivery system for dispensing a flowable substance, comprising:
   a source for storage of the flowable substance, the source having an opening;
   an actuator assembly coupled to the opening of the source and
   a valve assembly coupled to the actuator assembly, said valve assembly including
      (i) an inner core having an inlet opening for receiving the flowable substance into a passageway and at least one port opening from the passageway,
      (ii) a hollow flexible membrane having a first end and a second end, the first end being thicker than the second end, wherein the hollow flexible membrane is fitted over an outer surface of the inner core and when the flowable substance is placed under pressure the flowable substance exits through the at least one port opening and expands said membrane outwardly from said outer surface of said inner core; and
      (iii) a cover enclosing the flexible membrane and having an outlet orifice for dispensing the flowable substance from the valve assembly when pressure is applied to the flowable substance;
   wherein when the pressure on the flowable substance is released, the first end of the hollow flexible membrane moves back into tightly fitting contact with the outer surface of the inner core before the remainder of the hollow flexible membrane moves back into tightly fitting contact with the outer surface of said inner core, and
   wherein the actuator assembly comprises a traveling piston.

15. The valve assembly and delivery system as set forth in claim 14 wherein the actuator assembly includes a check valve coupled to the valve assembly and a button coupled to the traveling piston.

16. The valve assembly and delivery system as set forth in claim 14 wherein a check valve is located upstream from the source and wherein the check valve is actuated by a button located downstream of the source such that flowable substance exits the source, resulting in the delivery of a premeasured amount of flowable substance from the source.

17. The valve assembly and delivery system as set forth in claim 14 wherein the hollow flexible membrane has an axially extending uninterrupted continuous band at the first end of the hollow flexible membrane adjacent the outlet orifice in the cover and completely encircling the core.

18. The valve assembly and delivery system as set forth in claim 14, wherein the valve assembly, actuator assembly and source are coupled in fluid tight contact with each other.

19. A continuously sealing one way valve assembly and delivery system for dispensing a flowable substance, comprising:
   a source for storage of the flowable substance, the source having an opening;
   an actuator assembly coupled to the opening of the source and
   a valve assembly coupled to the actuator assembly, said valve assembly including
      (i) an inner core having an inlet opening for receiving the flowable substance into a passageway and at least one port opening from the passageway,
      (ii) a hollow flexible membrane having a first end and a second end, the first end being thicker than the second end, wherein the hollow flexible membrane is fitted over an outer surface of the inner core and when the flowable substance is placed under pressure the flowable substance exits through the at least one port opening and expands said membrane outwardly from said outer surface of said inner core; and
      (iii) a cover enclosing the flexible membrane and having an outlet orifice for dispensing the flowable substance from the valve assembly when pressure is applied to the flowable substance;
   wherein when the pressure on the flowable substance is released, the first end of the hollow flexible membrane moves back into tightly fitting contact with the outer surface of the inner core before the remainder of the hollow flexible membrane moves back into tightly fitting contact with the outer surface of said inner core and
   wherein one or more of said valve assembly, actuator assembly and source comprise an anti-microbial or water repelling substance.

\* \* \* \* \*